US009643927B1

(12) United States Patent
Sturdivant et al.

(10) Patent No.: US 9,643,927 B1
(45) Date of Patent: May 9, 2017

(54) PROCESS FOR THE PREPARATION OF KINASE INHIBITORS AND INTERMEDIATES THEREOF

(71) Applicant: Aerie Pharmaceuticals, Inc., Research Triangle Park, NC (US)

(72) Inventors: Jill M. Sturdivant, Chapel Hill, NC (US); Mitchell A. deLong, Chapel Hill, NC (US); Gilles Chambournier, Ann Arbor, MI (US); Michael G. Pamment, Ann Arbor, MI (US); Victor Fedij, Ypsilanti, MI (US)

(73) Assignee: Aerie Pharmaceuticals, Inc., Research Triangle Park, NC (US)

( * ) Notice: Subject to any disclaimer, the term of this patent is extended or adjusted under 35 U.S.C. 154(b) by 0 days.

(21) Appl. No.: 14/944,101

(22) Filed: Nov. 17, 2015

(51) Int. Cl.
| C07D 217/02 | (2006.01) |
| C07C 309/04 | (2006.01) |
| C07D 249/18 | (2006.01) |
| C07C 69/76 | (2006.01) |
| C07D 263/26 | (2006.01) |
| C07C 271/22 | (2006.01) |

(52) U.S. Cl.
CPC ............ *C07D 217/02* (2013.01); *C07C 69/76* (2013.01); *C07C 271/22* (2013.01); *C07C 309/04* (2013.01); *C07D 249/18* (2013.01); *C07D 263/26* (2013.01)

(58) Field of Classification Search
CPC .. C07D 215/38; C07D 217/02; C07D 263/26; C07D 249/18; A61K 31/04; C07C 69/76; C07C 271/22; C07C 309/04
See application file for complete search history.

(56) References Cited

U.S. PATENT DOCUMENTS

| 4,146,637 A | 3/1979 | Metz et al. |
| 4,337,256 A | 6/1982 | Suzuki et al. |
| 4,456,757 A | 6/1984 | Hidaka et al. |
| 4,709,032 A | 11/1987 | Hidaka et al. |
| 4,911,928 A | 3/1990 | Wallach |
| 4,954,512 A | 9/1990 | Oguro et al. |
| 5,508,288 A | 4/1996 | Forbes et al. |
| 5,519,036 A | 5/1996 | Himmelsbach et al. |
| 5,770,759 A | 6/1998 | Ueno et al. |
| 5,798,380 A | 8/1998 | Kaufman et al. |
| 5,889,052 A | 3/1999 | Klimko et al. |
| 5,891,646 A | 4/1999 | Barak et al. |
| 5,977,173 A | 11/1999 | Wos et al. |
| 5,994,397 A | 11/1999 | Selliah et al. |
| 6,025,392 A | 2/2000 | Selliah et al. |
| 6,030,999 A | 2/2000 | Stjernschantz et al. |
| 6,037,364 A | 3/2000 | Burk |
| 6,037,368 A | 3/2000 | Podos et al. |
| 6,048,895 A | 4/2000 | Wos et al. |
| 6,110,693 A | 8/2000 | Barak et al. |
| 6,110,912 A | 8/2000 | Kaufman et al. |
| 6,362,177 B1 | 3/2002 | Shiota et al. |
| 6,586,425 B2 | 7/2003 | Kaufman et al. |
| 6,699,891 B1 | 3/2004 | Kawanishi et al. |
| 6,787,534 B2 | 9/2004 | Haneda et al. |
| 7,268,143 B2 | 9/2007 | Jagtap et al. |
| 7,329,684 B2 | 2/2008 | Mjalli et al. |
| 7,345,158 B2 | 3/2008 | Egashira et al. |
| 7,361,678 B2 | 4/2008 | Mjalli et al. |
| 7,374,891 B2 | 5/2008 | Shahbaz |
| 7,378,498 B2 | 5/2008 | Worley et al. |
| 7,470,787 B2 | 12/2008 | deLong et al. |
| 7,671,205 B2 | 3/2010 | deLong et al. |
| 8,034,943 B2 | 10/2011 | deLong et al. |
| 8,129,411 B2 | 3/2012 | Ehara et al. |
| 8,357,699 B2 | 1/2013 | deLong et al. |
| 8,394,826 B2 * | 3/2013 | deLong ................. C07C 237/20 514/307 |
| 8,450,344 B2 | 5/2013 | deLong et al. |
| 8,455,513 B2 | 6/2013 | deLong et al. |
| 8,455,514 B2 | 6/2013 | deLong et al. |
| 8,455,647 B2 | 6/2013 | deLong et al. |
| 8,716,310 B2 * | 5/2014 | deLong ................. C07C 237/20 514/312 |
| 8,759,388 B2 | 6/2014 | deLong et al. |
| 8,809,326 B2 | 8/2014 | Bosanac et al. |
| 8,871,757 B2 | 10/2014 | deLong et al. |
| 8,921,392 B2 | 12/2014 | deLong et al. |
| 9,096,569 B2 | 8/2015 | deLong et al. |
| 2004/0091946 A1 | 5/2004 | Oakley et al. |
| 2004/0176462 A1 | 9/2004 | Kawanishi et al. |
| 2005/0032125 A1 | 2/2005 | Oakley et al. |

(Continued)

FOREIGN PATENT DOCUMENTS

| EP | 0109023 | 5/1984 |
| EP | 0232569 | 8/1987 |

(Continued)

OTHER PUBLICATIONS

Anonymous, "Aerie Pharmaceuticals, Inc. Gets Good News on Glaucoma Treatment" (Feb. 11, 2012) Retrieved from the Internet: URL:http://www.biospace.com.
Banker, G.S. et al., Modern Pharmaceutics, Marcel Dekker, Inc., New York, (1979) Chapters 9 and 10.
Berge et al, 1977, "Pharmaceutically Acceptable Salts." J. Pharm. Sci. vol. 66, pp. 1-19.
Bird, G.J. et al., "N-methyl as a bioisostere for the oxygen link between the aromatic rings of aryloxyphenoxypropionate herbicides," Bioorg. Med. Chem. Lett. (1997) 7:1489-1492.
Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters: evidence of a remote phenyl binding domain on the dopamine transporter". J. Med. Chem. 45 (18):4029-37.

(Continued)

*Primary Examiner* — D M Seaman
(74) *Attorney, Agent, or Firm* — Michael Best & Friedrich LLP

(57) ABSTRACT

Described are processes for the synthesis of certain compounds, useful for treating diseases, e.g. eye disease, such as glaucoma and ocular hypertension, in a subject.

22 Claims, No Drawings

(56) References Cited

U.S. PATENT DOCUMENTS

| | | | |
|---|---|---|---|
| 2005/0176712 A1 | 8/2005 | Wakabayashi et al. |
| 2005/0245509 A1 | 11/2005 | Nakajima et al. |
| 2005/0282805 A1 | 12/2005 | Hangeland et al. |
| 2006/0270670 A1 | 11/2006 | Chew et al. |
| 2007/0111983 A1 | 5/2007 | Fong |
| 2007/0123561 A1 | 5/2007 | Lee et al. |
| 2007/0129404 A1 | 6/2007 | Hagihara et al. |
| 2007/0135499 A1 | 6/2007 | deLong et al. |
| 2007/0149473 A1 | 6/2007 | Chatterton et al. |
| 2007/0149548 A1 | 6/2007 | Hellberg et al. |
| 2007/0167444 A1 | 7/2007 | Kuramochi et al. |
| 2007/0238741 A1 | 10/2007 | Nagarathnam et al. |
| 2008/0021026 A1 | 1/2008 | Kahraman et al. |
| 2008/0021217 A1 | 1/2008 | Borchardt |
| 2008/0058384 A1 | 3/2008 | Lee et al. |
| 2008/0096238 A1 | 4/2008 | Sharif et al. |
| 2008/0125427 A1 | 5/2008 | Sehon et al. |
| 2008/0139595 A1 | 6/2008 | Schirok et al. |
| 2008/0153799 A1 | 6/2008 | Laurent et al. |
| 2008/0153813 A1 | 6/2008 | Chen et al. |
| 2008/0194584 A1 | 8/2008 | Birault et al. |
| 2008/0275029 A1 | 11/2008 | Berdini et al. |
| 2009/0005321 A1 | 1/2009 | Zimmer et al. |
| 2009/0069371 A1 | 3/2009 | deLong et al. |
| 2010/0093790 A1 | 4/2010 | deLong et al. |
| 2010/0105650 A1 | 4/2010 | Plettenburg et al. |
| 2011/0015204 A1 | 1/2011 | Bencsik et al. |
| 2012/0135984 A1 | 5/2012 | deLong et al. |
| 2014/0187617 A1 | 7/2014 | deLong et al. |
| 2014/0275160 A1 | 9/2014 | Kopczynski |
| 2014/0275161 A1 | 9/2014 | Kopczynski |
| 2014/0288086 A1 | 9/2014 | Cui et al. |
| 2014/0357652 A1 | 12/2014 | Bosanac et al. |
| 2015/0119419 A1 | 4/2015 | deLong et al. |
| 2015/0175549 A1 | 6/2015 | deLong et al. |
| 2015/0297581 A1 | 10/2015 | Bosanac et al. |
| 2015/0299159 A1 | 10/2015 | deLong et al. |

FOREIGN PATENT DOCUMENTS

| | | |
|---|---|---|
| EP | 0389995 | 10/1990 |
| EP | 0482939 | 4/1992 |
| EP | 1541151 | 6/2005 |
| EP | 1550660 | 7/2005 |
| JP | 2005227441 | 8/2005 |
| JP | 2007236388 | 9/2007 |
| JP | 2007246466 | 9/2007 |
| WO | WO 93/18028 | 9/1993 |
| WO | WO 95/19964 | 7/1995 |
| WO | WO 96/10407 | 4/1996 |
| WO | WO 97/23223 | 7/1997 |
| WO | WO 98/12175 | 3/1998 |
| WO | WO 98/20880 | 5/1998 |
| WO | WO 98/20881 | 5/1998 |
| WO | WO 98/21180 | 5/1998 |
| WO | WO 98/21181 | 5/1998 |
| WO | WO 98/21182 | 5/1998 |
| WO | WO 98/39293 | 9/1998 |
| WO | WO 98/50024 | 11/1998 |
| WO | WO 98/57930 | 12/1998 |
| WO | WO 98/57942 | 12/1998 |
| WO | WO 99/02165 | 1/1999 |
| WO | WO 99/12895 | 3/1999 |
| WO | WO 99/12896 | 3/1999 |
| WO | WO 99/12898 | 3/1999 |
| WO | WO 99/25358 | 5/1999 |
| WO | WO 99/26629 | 6/1999 |
| WO | WO 99/32441 | 7/1999 |
| WO | WO 00/03736 | 1/2000 |
| WO | WO 00/03980 | 1/2000 |
| WO | WO 00/76970 | 12/2000 |
| WO | WO 01/37826 | 5/2001 |
| WO | WO 01/47891 | 7/2001 |
| WO | WO 01/53268 | 7/2001 |
| WO | WO 01/53274 | 7/2001 |
| WO | WO 01/56607 | 8/2001 |
| WO | WO 02/22576 | 3/2002 |
| WO | WO 02/32864 | 4/2002 |
| WO | WO 02/085857 | 10/2002 |
| WO | WO 02/085859 | 10/2002 |
| WO | WO 03/064397 | 8/2003 |
| WO | WO 03/073999 | 9/2003 |
| WO | WO 03/080578 | 10/2003 |
| WO | WO 2004/029045 | 4/2004 |
| WO | WO 2004/078747 | 9/2004 |
| WO | WO 2005/020921 | 3/2005 |
| WO | WO 2005/035503 | 4/2005 |
| WO | WO 2005/037257 | 4/2005 |
| WO | WO 2006/041119 | 4/2006 |
| WO | WO 2006/051290 | 5/2006 |
| WO | WO 2006/062982 | 6/2006 |
| WO | WO 2006/076706 | 7/2006 |
| WO | WO 2007/008926 | 1/2007 |
| WO | WO 2007/008942 | 1/2007 |
| WO | WO 2007/060028 | 5/2007 |
| WO | WO 2007/065916 | 6/2007 |
| WO | WO 2007/076360 | 7/2007 |
| WO | WO 2007/076367 | 7/2007 |
| WO | WO 2007/100880 | 9/2007 |
| WO | WO 2007/142323 | 12/2007 |
| WO | WO 2008/011557 | 1/2008 |
| WO | WO 2008/011560 | 1/2008 |
| WO | WO 2008/016016 | 2/2008 |
| WO | WO 2008/036459 | 3/2008 |
| WO | WO 2008/036540 | 3/2008 |
| WO | WO 2008/049000 | 4/2008 |
| WO | WO 2008/049919 | 5/2008 |
| WO | WO 2008/054599 | 5/2008 |
| WO | WO 2008/077057 | 6/2008 |
| WO | WO 2008/077550 | 7/2008 |
| WO | WO 2008/077551 | 7/2008 |
| WO | WO 2008/077552 | 7/2008 |
| WO | WO 2008/077553 | 7/2008 |
| WO | WO 2008/077554 | 7/2008 |
| WO | WO 2008/077555 | 7/2008 |
| WO | WO 2008/077556 | 7/2008 |
| WO | WO 2008/079880 | 7/2008 |
| WO | WO 2008/079945 | 7/2008 |
| WO | WO 2008/086269 | 7/2008 |
| WO | WO 2008/124665 | 10/2008 |
| WO | WO 2009/091898 | 7/2009 |
| WO | WO 2010/011853 | 1/2010 |
| WO | WO 2010/126626 | 11/2010 |
| WO | WO 2010/127329 | 11/2010 |
| WO | WO 2010/127330 | 11/2010 |
| WO | WO 2012/105674 | 8/2012 |

OTHER PUBLICATIONS

C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.

Calmes et al., Eur. J. Org. Chem. 2000, 2459-2466.

"Cancer", MedlinePlus (retrieved Jul. 6, 2007) 10 pages, http://www.nlm.nih.gov/medlineplus/cancer.html.

Capdeville, R. et al., "Glivec (STI571, IMATINIB), A Rationally Developed, Targeted Anticancer Drug", Nature Reviews Drug Discovery (2002) 1:493-502.

Chen, P. et al., "Identification of novel and potent isoquinoline aminooxazole-based IMPDH inhibitors," Bioorg. Med. Chem. Lett. (2003) 13(7):1345-1348.

Cheung, S.T. et al. Can. J. Chem. 1977, 55,906-910.

Dancey, J. et al., "Issues and Progress with Protein Kinase Inhibitors for Cancer Treatment", Nature Reviews Drug Discovery (2003) 2:296-313.

deLong et al., "Discovery and SAR of a Class of Ocularly-active Compounds Displaying a Dual Mechanism of Activity for the Treatment of Glaucoma" (May 6, 2012) Retreived from the Internet: URL:http://www.aeriepharma.com.

Dorwald, F.Z., Side Reactions in Organic Synthesis. A Guide to Successful Synthesis Design, Wiley-VCH, Weinheim (2005) IX of Preface and 1-15.

(56) References Cited

OTHER PUBLICATIONS

Dowton et al., "Influence of Liposomal Composition on Topical Delivery of Encapsulated Cyclosporin A", S.T.P. Pharma Sciences, vol. 3, pp. 404-407 (1993).
Foye, Foye's Principles of Medicinal Chemistry, 5th Edition (2002) Lippencott, Williams, Wilkins, p. 59-63.
Gingras et al., "In Synthesis and evaluation of 4-(1-aminoalkyl)-N-(4-pyridyl)-cyclohexanecarboxamides as Rho-kinase inhibitors and neurite outgrowth promoters," Bioorganic & Medicinal Chemistry Letters, 2004, vol. 14, pp. 4931-4934.
Golub, T.R. et al., "Molecular classification of cancer: class discovery and class prediction by gene expression monitoring," Science (1999) 286:531-537.
Hackam, A.S. et al., "The WNT Signaling Pathway in Retinal Degenerations", IUBMB Life (2005) 57(6):381-388.
Hazeldine, S.T. et al., "II. Synthesis and biological evaluation of some bioisosteres and cogeners of the antitumour agent, 2{4[7-chloro-2-quinoxalinyl)oxy]phenoxy}propionic acid (XK469)," J. Med. Chem. (2002) 45:3130-3137.
He R, Kurome T, Giberson KM, Johnson KM, Kozikowski AP (2005). "Further structure-activity relationship studies of piperidine-based monoamine transporter inhibitors: effects of piperidine ring stereochemistry on potency. Identification of norepinephrine transporter selective ligands and broad-spectrum transporter inhibitors". J. Med. Chern. 48 (25): 7970-9.
Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.
Helzner, "Bright New Ideas in Glaucoma Treatment" (2013) Retreived from the Internet: URL:http://mydigimag.rrd.com.
Hu, E. et al., "Rho kinase as potential therapeutic target for cardiovascular diseases: opportunities and challenges," Exp. Opin. Ther. Targets (2005) 9:715-736.
Inouye, Y. et al., "The Absolute Configurations of Trans-1,2-Cyclopropanedicarboxylic Acid and Trans-2-Phenylcyclopropanecarboxylic Acid", Int'l. J. Org. Chem. (1964) 20(5):1695-1699.
Ito, N. et al., "A medium-term rat liver bioassay for rapid in vivo detection of carcinogenic potential of chemicals," Cancer Science, Jan. 2003, vol. 94, No. 1, pp. 3-8.
Jacobs, M. et al., "The structure of dimeric ROCK I reveals the mechanism for ligand selectivity," J. Bio. Chem., 2006, pp. 260-268, published on Jan. 6, 2006.
Karaman, M.W. et al., "A quantitative analysis of kinase inhibitor selectivity," Nature Biotech. (2008) 26(1):127-132.
Katritzky, A.R. et al., "Benzotriazole mediated amino-, amido-, alkoxy- and alkylthio-alkylation," Tetrahedron (2005) 61:2555-2581.
Lala, P.K. et al., "Role of nitric oxide in tumor progression: lessons from experimental tumors," Cancer and Metastasis Reviews (1998) 17:91-106.
Liljebris, C. et al., "Derivatives of 17-Phenyl-18,19,20-trinorprostaglandin F2α Isopropyl Ester: Potential Antiglaucoma Agents," J. Med. Chem. (1995) 38(2):289-304.
Loge, C; Siomboing, X et al. J, of Enzy Inhib & Med Chem, 2003,18,127-128.
Matsui, T. et al., "Novel 5-HT3 antagonists. Isoquinolinones and 3-aryl-2-pyridones," J. Med. Chem. (1992) 35:3307-3319.
McCutcheon's, "Emulsifiers & Detergents", North American Edition (1994) vol. 1:236-239.
Meanwell, "Synopsis of some recent tactical application of bioisosteres in drug design," J. Med. Chem., 2011, vol. 54, pp. 2529-2591.
Nakanishi et al. FEBS Letters 368, (1995) 411-414.
Oakley, R.H. et al. "The Cellular Distribution of Fluorescently Labeled Arrestins Provides a Robust, Sensitive and Universal Assay for Screening G Protein-Coupled Receptors," Assay and Drug Development Technologies (2002) 1(1-1):21-30.

Olson, "Application for ROCK kinase inhibition," Current Opinion in Cell Biology, 2008, vol. 20, pp. 242-248.
Parang, K. et al., "Design strategies for protein kinase inhibitors," Curr. Opin. in Drug Disc. & Dev. (2004) 7(5):617-629.
Pardridge, "The Blood-Brain Barrier: Bottleneck in Brain Drug development," J. Am. Soc. Exper. NeuroTherapeutics, 2005, vol. 2, p. 3-14.
Penmetsa, K.V. et al., "Development of Reversed-Phase Chiral HPLC Methods Using Mass Spectrometry Compatible Mobile Phases", J. Liquid Chroma. Rel. Tech. (2000) 23(6-10):831-839.
Penn, R.B. et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. (1999) 288(2):428-437.
Pharmasolve (N-Methyl-2-Pyrrolidone) product spcification, International Specialty Products, 2000, 10 pages.
PubChem, AC1NQAJU (compound sumary for CID 5172372) '372' date created: Sep. 26, 2005 date access: Jan. 5, 2016, 10 pages.
Rashid et al., "Development of Rho-kinase inhibitors for cardiovascular medicine," Trends in Pharmacological Science, 2007, vol. 28, pp. 296-302.
Shankar, G. et al., "Protein-kinase-specific inhibitors block Langerhans' cell migration by inhibiting interleukin-1α release", Immunology (1999) 96:230-235.
Stirewalt, D.L. et al., "The Role of FLT3 in Haematopoietic Malignancies", Nature Reviews Cancer (2003) 3:650-665.
STN Registry Database entry for CAS RN 309903-43-6, Published in database Dec. 20, 2000.
Tamura, M., et al., "Development of specific Rho-kinase inhibitors and their clinical application," Biochimica et Biophysica Acta, 2005, vol. 1754, pp. 245-252.
Torres, G.E. et al. (2003). "Plasma membrane monoamine transporters: structure, regulation and function". Nat. Rev. Neurosci. 4 (1): 13-25.
Van Muijlwijk-Koezen et al., "A novel class of adenosine A3 receptor-ligands. 2. Structure affinity profile of a series of isoquinoline and quinazoline compounds," J. Med. Chem. (1998) 41:3994-4000.
Vippagunta et al., "Cystalline solids," 2001, Advanced Drug Delivery Reviews, 48, pp. 3 and 18.
Wallach and Philippot, "New Type of Lipid Vesicle: Novasome®", Liposome Technology, vol. 1, pp. 141-156 (1993).
Webster, F.X. et al., "Following the Course of Resolution of Carboxylic Acids by 13C NMR Spectrometry of Amine Salts" J. Org. Chem. (1982) 47(26):5225-5226.
West, A.R., "Solid state chemistry and its applications," Wiley, New York (1988) pp. 358 and 365.
Westaway, S.M. et al., "N-tetrahydroquinolinyl, N-quinolinyl and N-isoquinolinyl biaryl carboxamides as antagonists of TRPV1," Biorg. Med. Chem. Lett. (2006) 16:4533-4536.
Westra, J. et al., "p38 Mitogen-Activated Protein Kinase (MAPK) in Rheumatoid Arthritis", Mini-Reviews in Medicinal Chemistry (2006) 6(8):867-874.
Yamashita et al., "The therapeutic effects of Rho-Rock inhibitors on CNS disorder," Therapeutics and Clinical Risk Management, 2008, vol. 4, pp. 605-615.
United States Office Action for U.S. Appl. No. 11/485,182 dated Apr. 16, 2009 (13 pages).
United States Office Action for U.S. Appl. No. 12/274,887 dated Jun. 16, 2009 (11 pages).
United States Patent Office Action for U.S. Appl. No. 12/639,670 dated Jan. 31, 2011 (8 pages).
United States Patent Office Action for U.S. Appl. No. 12/639,670 dated Jul. 27, 2011 (5 pages).
United States Patent Office Action for U.S. Appl. No. 11/621,887 dated May 18, 2010 (8 pages)
United States Patent Office Action for U.S. Appl. No. 11/621,887 dated Oct. 29, 2010 (14 pages).
United States Patent Office Action for U.S. Appl. No. 13/017,708 dated Apr. 3, 2012 (11 pages).
United States Patent Office Notice of Allowance for U.S. Appl. No. 13/017,708 dated Sep. 17, 2012 (8 pages).

(56) References Cited

OTHER PUBLICATIONS

United States Patent Office Notice of Allowance for U.S. Appl. No. 13/017,708 dated Oct. 23, 2012 (7 pages).
United States Patent Office Notice of Allowability for U.S. Appl. No. 13/017,708 dated Dec. 12, 2012 (5 pages).
United States Patent Office Notice of Allowance for U.S. Appl. No. 11/621,887 dated Feb. 27, 2013 (8 pages).
United States Patent Office Action for U.S. Appl. No. 13/723,811 dated Jan. 27, 2014 (8 pages).
United States Patent Office Action for U.S. Appl. No. 13/723,811 dated Jun. 17, 2014 (6 pages).
United States Patent Office Notice of Allowance for U.S. Appl. No. 13/723,811 dated Aug. 19, 2014 (11 pages).
United States Patent Office Action for U.S. Appl. No. 14/583,439 dated Jun. 23, 2015 (6 pages).
United States Patent Office Action for U.S. Appl. No. 14/583,439 dated Oct. 30, 2015 (7 pages).
United States Patent Office Notice of Allowance for U.S. Appl. No. 14/583,439 dated Feb. 12, 2016 (8 pages).
United States Office Action for U.S. Appl. No. 11/621,892 dated Aug. 8, 2008 (9 pages).
United States Office Action for U.S. Appl. No. 11/621,892 dated Mar. 9, 2009 (6 pages).
United States Patent Office Action for U.S. Appl. No. 12/701,963 dated May 10, 2011 (3 pages).
United States Patent Office Action for U.S. Appl. No. 13/230,105 dated Mar. 5, 2012 (8 pages).
United States Patent Office Final Rejection for U.S. Appl. No. 13/230,105 dated Jul. 9, 2012 (11 pages).
United States Patent Office Notice of Allowance for U.S. Appl. No. 13/230,105 dated Mar. 19, 2013 (5 pages).
United States Patent Office Action for U.S. Appl. No. 12/009,326 dated Feb. 3, 2011 (8 pages).
United States Patent Office Notice of Allowance for U.S. Appl. No. 12/009,326 dated Jan. 6, 2012 (5 pages).
United States Patent Office Notice of Allowance for U.S. Appl. No. 12/009,326 dated Feb. 25, 2013 (8 pages).
United States Patent Office Action for U.S. Appl. No. 12/704,822 dated Apr. 30, 2012 (34 pages).
United States Patent Office Final Rejection for U.S. Appl. No. 12/704,822 dated Jan. 16, 2013 (16 pages).
United States Patent Office Action for U.S. Appl. No. 12/704,822 dated Oct. 10, 2013 (11 pages).
United States Patent Office Action for U.S. Appl. No. 12/704,822 dated May 8, 2014 (13 pages).
United States Patent Office Notice of Allowance for U.S. Appl. No. 12/704,822 dated Sep. 9, 2014 (11 pages).
United States Patent Office Advisory Action for U.S. Appl. No. 11/856,740 dated Feb. 10, 2011 (3 pages).
United States Patent Office Action for U.S. Appl. No. 11/856,740 dated Dec. 6, 2010 (12 pages).
United States Patent Office Action for U.S. Appl. No. 11/856,740 dated Jun. 29, 2010 (10 pages).
United States Patent Office Action for U.S. Appl. No. 12/180,259 dated Jul. 5, 2011 (11 pages).
United States Patent Office Notice of Allowance for U.S. Appl. No. 12/180,259 dated Dec. 19, 2011 (6 pages).
United States Patent Office Notice of Allowance for U.S. Appl. No. 13/442,263 dated Dec. 19, 2012 (13 pages).
United States Patent Office Notice of Allowance for U.S. Appl. No. 13/442,263 dated Feb. 25, 2013 (8 pages).
United States Patent Office Notice of Allowance for U.S. Appl. No. 13/442,263 dated Jun. 12, 2013 (8 pages).
United States Patent Office Final Rejection for U.S. Appl. No. 13/442,263 dated Dec. 6, 2013 (8 pages).
United States Patent Office Notice of Allowance for U.S. Appl. No. 13/442,263 dated Apr. 15, 2014 (8 pages).
United States Patent Office Action for U.S. Appl. No. 14/273,895 dated Aug. 20, 2014 (8 pages).
United States Patent Office Action for U.S. Appl. No. 14/273,895 dated Dec. 24, 2014 (7 pages).
United States Patent Office Notice of Allowance for U.S. Appl. No. 14/273,895 dated Apr. 1, 2015 (8 pages).
United States Patent Office Action for U.S. Appl. No. 14/790,376 dated Jan. 22, 2016 (14 pages).
United States Patent Office Action for U.S. Appl. No. 13/318,457 dated Jun. 6, 2013 (12 pages).
United States Patent Office Final Rejection for U.S. Appl. No. 13/318,457 dated Nov. 27, 2013 (13 pages).
United States Patent Office Action for U.S. Appl. No. 12/694,965 dated May 17, 2012 (13 pages).
United States Patent Office Notice of Allowance for U.S. Appl. No. 12/694,965 dated Nov. 2, 2012 (8 pages).
United States Patent Office Notice of Allowance for U.S. Appl. No. 12/694,965 dated Nov. 19, 2012 (4 pages).
United States Patent Office Notice of Allowance for U.S. Appl. No. 13/768,594 dated Oct. 29, 2013 (7 pages).
United States Patent Office Action for U.S. Appl. No. 13/768,594 dated Jul. 10, 2013 (14 pages).
United States Patent Office Action for U.S. Appl. No. 14/138,592 dated Jul. 28, 2014 (17 pages).
United States Patent Office Action for U.S. Appl. No. 14/138,592 dated Dec. 9, 2014 (14 pages).
United States Patent Office Action for U.S. Appl. No. 11/856,740 dated Aug. 16, 2013 (14 pages).
United States Patent Office Notice of Allowance for U.S. Appl. No. 11/856,740 dated Apr. 1, 2014 (8 pages).
United States Patent Office Action for U.S. Appl. No. 14/461,597 dated Jan. 30, 2015 (19 pages).
United States Patent Office Action for U.S. Appl. No. 14/641,962 dated Sep. 22, 2015 (16 pages).
United States Patent Office Action for U.S. Appl. No. 14/754,787 dated Oct. 30, 2015 (20 pages).
United States Patent Office Action for U.S. Appl. No. 14/213,940 dated Oct. 29, 2015 (33 pages).
United States Patent Office Action for U.S. Appl. No. 14/213,961 dated Oct. 30, 2015 (37 pages).
Partial International Search for Application No. PCT/US2009/031117 dated Apr. 16, 2009 (4 pages).
International Search Report and Written Opinion for Application No. PCT/US2006/026976 dated Feb. 15, 2007 (14 pages).
International Search Report for Application No. PCT/US2006/026947 dated Nov. 17, 2006 (4 pages).
International Preliminary Examination Report for Application No. PCT/US2006/026947 dated Jan. 24, 2008 (10 pages).
International Search Report for Application No. PCT/US08/50374 dated Oct. 28, 2008 (7 pages).
International Preliminary Report on Patentability for Application No. PCT/US08/50374 dated Jul. 14, 2009 (12 pages).
International Search Report and Written Opinion for Application No. PCT/US2009/031117 dated Sep. 24, 2009 (13 pages).
Invitation to Pay Additional Fees and Partial International Search Report for International Application No. PCT/US2009/051569 dated Oct. 15, 2009 (4 pages).
International Search Report and Written Opinion for Application No. PCT/US2009/051569 dated May 20, 2010 (11 pages).
International Search Report and Written Opinion for Application No. PCT/US2010/33316 dated Jul. 14, 2010 (10 pages).
International Search Report and Written Opinion for Application No. PCT/US2010/33317 dated Aug. 17, 2010 (10 pages).
International Search Report and Written Opinion for Application No. PCT/US2010/022246 dated Nov. 10, 2010 (7 pages).
International Search Report and Written Opinion for Application No. PCT/US2007/078343 dated Apr. 3, 2008 (12 pages).
International Search Report and Written Opinion for Application No. PCT/US2014/029335, dated Jul. 2, 2014 (11 pages).
International Search Report and Written Opinion for Application No. PCT/US2015/61177 dated Feb. 2, 2016 (16 pages).
United States Patent Office Notice of Allowance for U.S. Appl. No. 14/790,376 dated Aug. 2, 2016 and Aug. 19, 2016 (10 pages).

(56) References Cited

OTHER PUBLICATIONS

United States Patent Office Action for U.S. Appl. No. 15/076,216 dated Sep. 1, 2016 (6 pages).
United States Patent Office Notice of Allowance for U.S. Appl. No. 14/213,961 dated Jun. 20, 2016 (8 pages).

* cited by examiner

PROCESS FOR THE PREPARATION OF KINASE INHIBITORS AND INTERMEDIATES THEREOF

TECHNICAL FIELD

The present disclosure relates to a process for preparing compounds according to Formula (I). These compounds are useful for treating diseases and disorders of the eye, such as glaucoma and ocular hypertension, of the respiratory system, of the cardiovascular system, of the skin, and for diseases characterized by abnormal growth, such as cancers.

BACKGROUND

There exists a need for processes to make the compounds disclosed herein in at least one or more of an efficient, scaleable, and reproducible manner that will allow for the generation of large scale quantities.

SUMMARY OF THE INVENTION

In one aspect, disclosed is a method of synthesizing a compound of Formula (I):

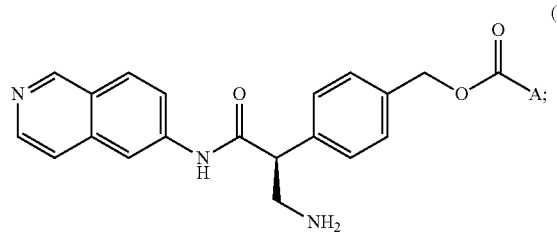

(I)

or a pharmaceutically acceptable salt thereof; wherein A is cyclohexyl or phenyl, substituted with 0-3 substituents selected from the group consisting of alkyl, halogen, alkoxy, and cyano;
comprising:
  (a) reacting a compound of Formula (II), wherein PG is a nitrogen protecting group,

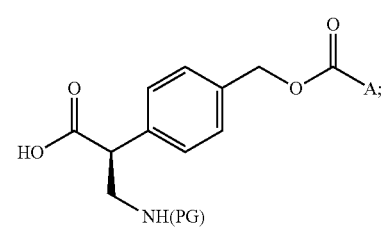

(II)

with 6-aminoisoquinoline to form a compound of Formula (III)

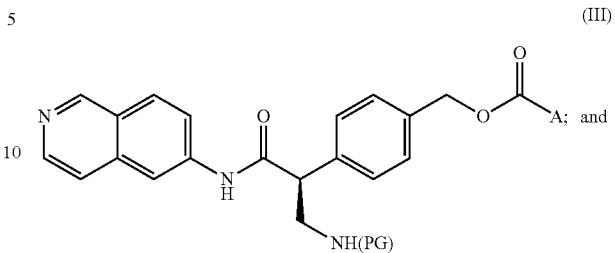

(III)

(b) removing the nitrogen protecting group to form the compound of formula (I).

In another aspect, disclosed is a method of synthesizing a compound of formula (I-a):

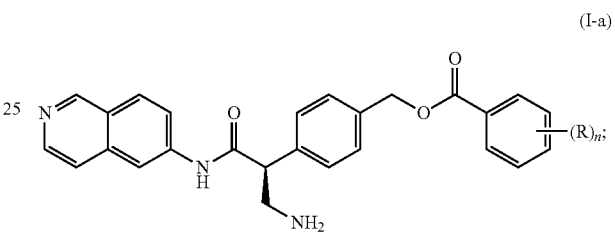

(I-a)

or a pharmaceutically acceptable salt thereof; wherein each R is independently selected from the group consisting of $C_{1-4}$ alkyl, halogen, $C_{1-4}$ alkoxy and cyano; and n is an integer from 0 to 3;
comprising:
  (a) reacting a compound of formula (II-a),

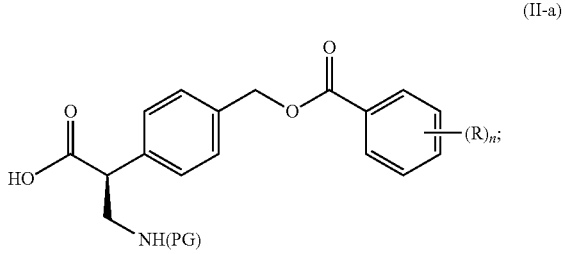

(II-a)

with 6-aminoisoquinoline to form a compound of formula (III-a),

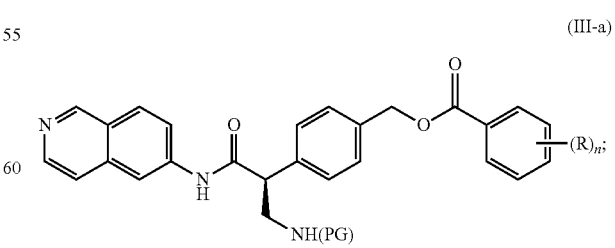

(III-a)

wherein each R is independently selected from the group consisting of $C_{1-4}$ alkyl, halogen, $C_{1-4}$ alkoxy and cyano; and n is an integer from 0 to 3; and (b) removing the nitrogen protecting group to form the compound of formula (I-a).

In another aspect, disclosed is a method of synthesizing a compound of Formula (XI):

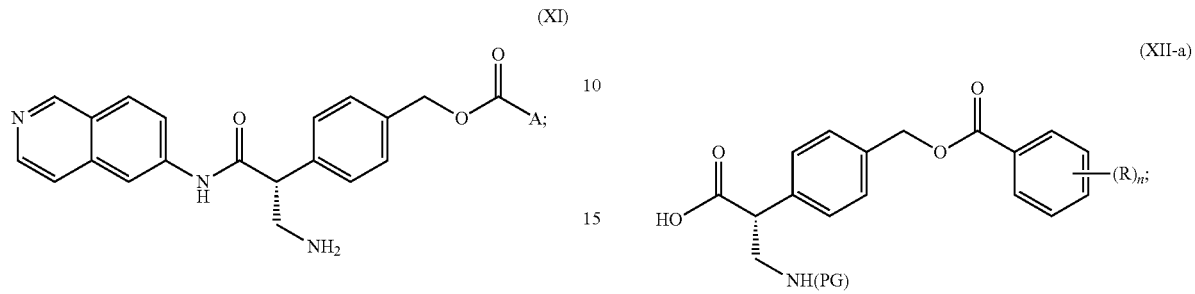

or a pharmaceutically acceptable salt thereof; wherein A is cyclohexyl or phenyl, substituted with 0-3 substituents selected from the group consisting of alkyl, halogen, alkoxy, and cyano;

comprising:
(a) reacting a compound of Formula (XII), wherein PG is a nitrogen protecting group,

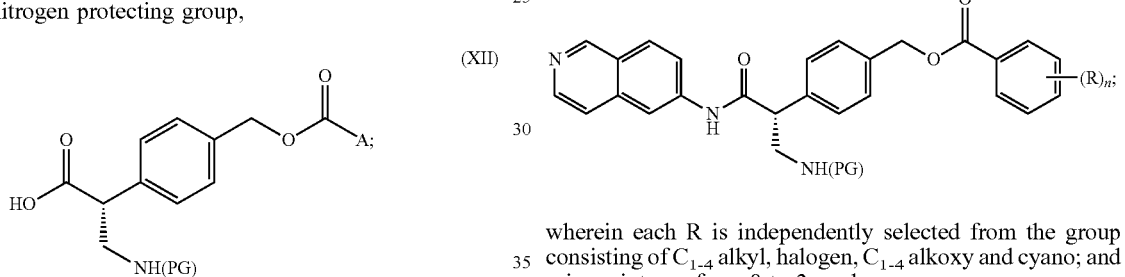

with 6-aminoisoquinoline to form a compound of Formula (XIII)

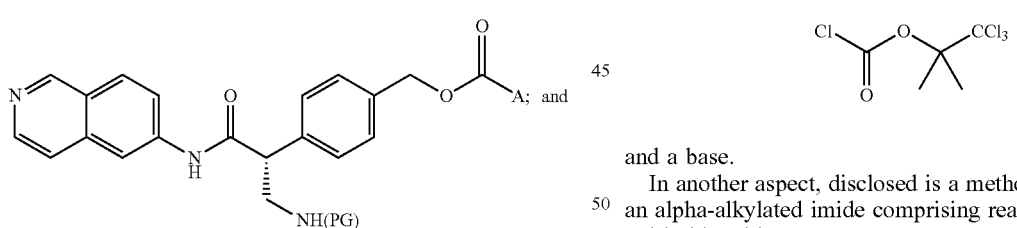

(b) removing the nitrogen protecting group to form the compound of formula (XI).

In another aspect, disclosed is a method of synthesizing a compound of formula (XI-a):

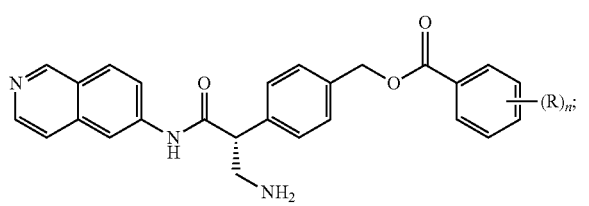

or a pharmaceutically acceptable salt thereof; wherein each R is independently selected from the group consisting of $C_{1-4}$ alkyl, halogen, $C_{1-4}$ alkoxy and cyano; and n is an integer from 0 to 3;

comprising:
(a) reacting a compound of formula (XII-a), (XII-a)

with 6-aminoisoquinoline to form a compound of formula (XIII-a), (XIII-a)

wherein each R is independently selected from the group consisting of $C_{1-4}$ alkyl, halogen, $C_{1-4}$ alkoxy and cyano; and n is an integer from 0 to 3; and
(b) removing the nitrogen protecting group to form the compound of formula (XI-a).

In another aspect, disclosed is a method for formation of an amide or ester bond comprising reacting an amine or alcohol with a carboxylic acid in the presence of and a base.

In another aspect, disclosed is a method for synthesizing an alpha-alkylated imide comprising reacting an oxazolidinyl imide with

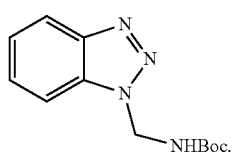 [SMILES: CC(C)(C)OC(=O)NCn1nnc2ccccc21]

In another aspect, disclosed are various intermediates for use in the claimed methods.

DETAILED DESCRIPTION

Disclosed herein are processes for the synthesis compounds of formula (I). Compounds of formula (I) may by synthesized in a manner that efficiently generates large scale quantities of the compound of formula (I). Compounds of formula (I) can be used to treat or prevent kinase-related diseases and/or disorders. These include diseases and disorders of the eye, such as glaucoma and ocular hypertension, of the respiratory system, of the cardiovascular system, of the skin, and for diseases characterized by abnormal growth, such as cancers.

1. Definitions

Unless otherwise defined, all technical and scientific terms used herein have the same meaning as commonly understood by one of ordinary skill in the art. In case of conflict, the present document, including definitions, will control. Suitable methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry,* 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3rd Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_{1-6}$-alkyl" means a straight or branched chain hydrocarbon containing from 1 to 6 carbon atoms. The term "$C_{3-7}$ branched alkyl" means a branched chain hydrocarbon containing from 3 to 7 carbon atoms. The term "$C_{1-4}$-alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. An alkyl group can be substituted or unsubstituted.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH$═—. An alkylene group can be substituted or unsubstituted.

The term "alkenyl" as used herein, means a straight or branched, unsaturated hydrocarbon chain containing at least one carbon-carbon double bond and from 1 to 10 carbon atoms. The term "lower alkenyl" or "$C_{2-6}$-alkenyl" means a straight or branched chain hydrocarbon containing at least one carbon-carbon double bond and from 1 to 6 carbon atoms. An alkenyl group can be substituted or unsubstituted.

The term "alkoxyalkyl" as used herein, refers to an alkoxy group, as defined herein, appended to the parent molecular moiety through an alkyl group, as defined herein.

The term "alkynyl" as used herein, means a straight or branched, unsaturated hydrocarbon chain containing at least one carbon-carbon triple bond and from 1 to 10 carbon atoms. The term "lower alkynyl" or "$C_{2-6}$-alkynyl" means a straight or branched chain hydrocarbon containing at least one carbon-carbon triple bond and from 1 to 6 carbon atoms. An alkynyl group can be substituted or unsubstituted.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl. An aryl group can be substituted or unsubstituted.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. A cycloalkyl group can be substituted or unsubstituted.

The term "cycloalkenyl" as used herein, refers to a carbocyclic ring system containing three to ten carbon atoms, zero heteroatoms and at least one double bond. A cycloalkenyl group can be substituted or unsubstituted.

The term "fluoroalkyl" as used herein, refers to at least one fluorine atom appended to the parent molecular moiety through an alkyl group, as defined herein. Representative examples of fluoroalkyl include, but are not limited to, trifluoromethyl.

The term "fluoroalkoxy" as used herein, refers to at least one fluorine atom appended to the parent molecular moiety through an alkoxy group, as defined herein.

The term "alkoxyfluoroalkyl" as used herein, refers to an alkoxy group, as defined herein, appended to the parent molecular moiety through a fluoroalkyl group, as defined herein.

The term "halogen" or "halo" as used herein, means Cl, Br, I, or F.

The term "haloalkyl" as used herein, refers to at least one halogen atom appended to the parent molecular moiety through an alkyl group, as defined herein.

The term "heteroalkyl" as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides. A heteroalkyl group can be substituted or unsubstituted.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, thiazolyl, isoquinolinyl, and quinolinyl. A heteroaryl group can be substituted or unsubstituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of 0, N, and S. The three- or four-membered ring contains zero or one double bond, and one heteroatom selected from the group consisting of 0, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of 0, N, and S. The seven- and eight-membered rings contains zero, one, two, or three double bonds and one, two, or three heteroatoms selected from the group consisting of 0, N, and S. A heterocylic group can be substituted or unsubstituted.

The term "heteroarylalkyl" as used herein, refers to a heteroaryl group, as defined herein, appended to the parent molecular moiety through an alkyl group, as defined herein.

The term "hydroxyalkyl" as used herein, refers to a hydroxy group appended to the parent molecular moiety through an alkyl group, as defined herein The term "arylalkyl" as used herein, refers to an aryl group, as defined herein, appended to the parent molecular moiety through an alkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "aromatic amine" refers to ArN(R)H, wherein R is H or $C_{1-4}$ alkyl.

The term "aromatic alcohol" refers to ROH, wherein R is an aryl group.

The term "substituents" refers to a group "substituted" on group at any atom of that group. Any atom can be substituted.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Process

A. Compound of Formula (I)

In one aspect, disclosed is a process for the synthesis of the compound of formula (I):

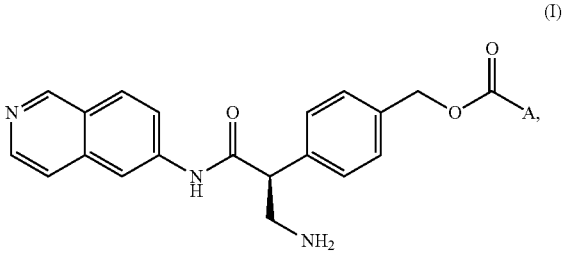

or a pharmaceutically acceptable salt thereof; wherein A is cyclohexyl or phenyl, substituted with 0-3 substituents independently selected from the group consisting of alkyl, halogen, alkoxy, and cyano.

In one embodiment, a process is provided that comprises reacting 6-aminoisoquinoline with the compound of formula (II), wherein PG is a protecting group for the nitrogen, to form the compound of formula (III). The compound of formula (III) can be transformed to the compound of formula (I) by removal of the nitrogen protecting group. The nitrogen protecting group, PG, may be any suitable nitrogen protecting group known in the art. In certain embodiments, PG is selected from the group consisting of tert-butyloxycarbonyl (Boc), carbobenzyloxy (CBZ), and para-methoxybenzyl carbonyl (Moz).

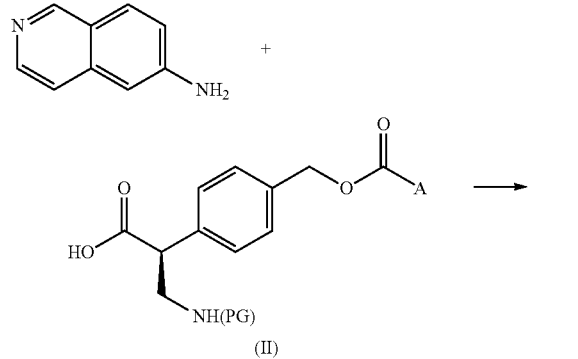

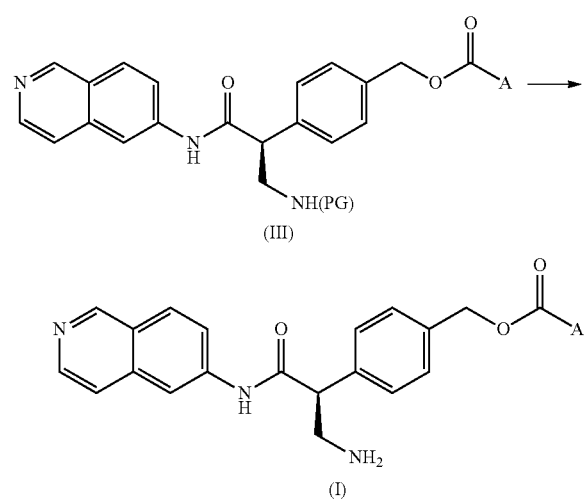

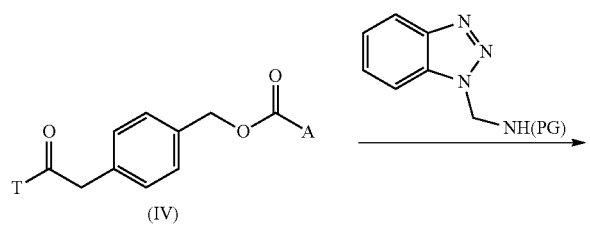

In some embodiments, the synthesis of the compound of formula (II) may also be included. Aminoalkylation of the compound of formula (IV), wherein T is a chiral auxiliary, can provide the compound of formula (V), which can be converted to the compound of formula (II) upon removal of the chiral auxiliary.

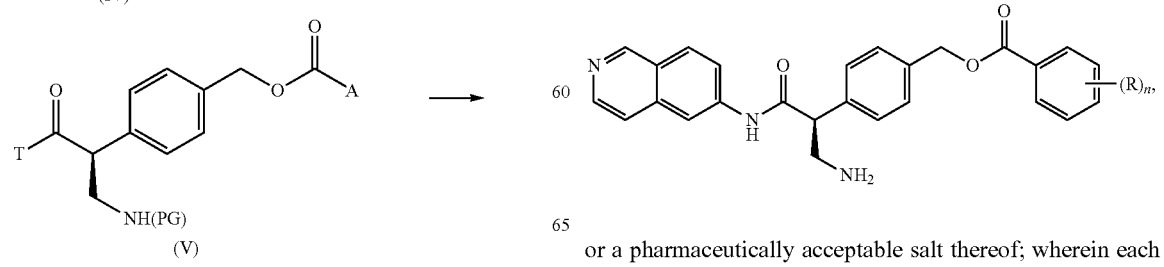

In some embodiments, the compound of formula (VII) can be prepared by reaction of methyl 2-(4-(hydroxymethyl)phenyl)acetate with the compound of formula (VI) may also be included. The compound of formula (VII) can be converted to the compound of formula (VIII), wherein $R^1$ is is halogen, $OR^a$, $OC(O)R^b$, $SR^a$, or $SC(O)R^b$; wherein $R^a$ is H, alkyl or aryl, and $R^b$ is alkyl or aryl. The compound of formula (IV) can be obtained in turn from the compound of formula (VIII), wherein T is a chiral auxiliary.

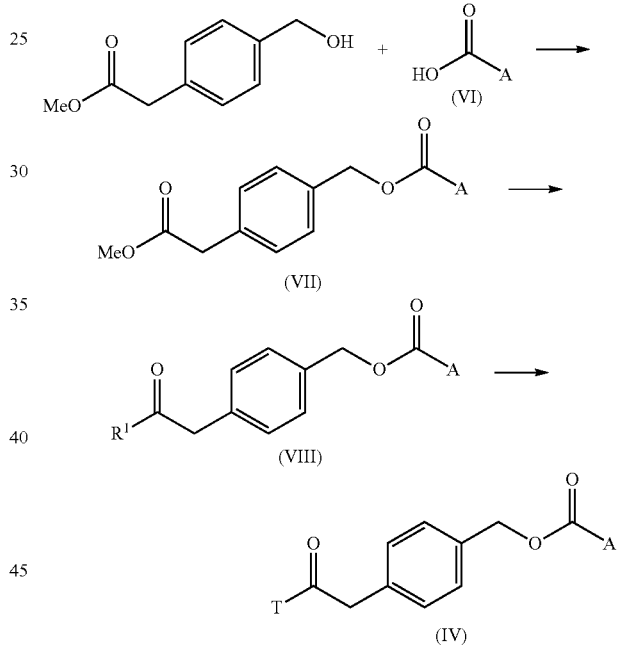

B. Compound of Formula (I-a)

In an embodiment, a synthesis for the compound of formula (I-a) is provided:

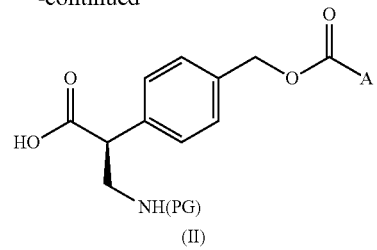

or a pharmaceutically acceptable salt thereof; wherein each R is independently selected from the group consisting of $C_{1-4}$ alkyl, halogen, $C_{1-4}$ alkoxy and cyano; and n is an integer from 0 to 3. In some embodiments, the $C_{1-4}$ alkyl may be a $C_{1-4}$ fluoroalkyl.

The process includes reacting 6-aminoisoquinoline with the compound of formula (II-a), wherein PG is a protecting group for the nitrogen, to form the compound of formula (III-a). The compound of formula (III-a) can be transformed to the compound of formula (I-a) by removal of the nitrogen protecting group. The nitrogen protecting group, PG, may be any suitable nitrogen protecting group known in the art. In certain embodiments, PG is selected from the group consisting of tert-butyloxycarbonyl (Boc), carbobenzyloxy (CBZ), and para-methoxybenzyl carbonyl (Moz).

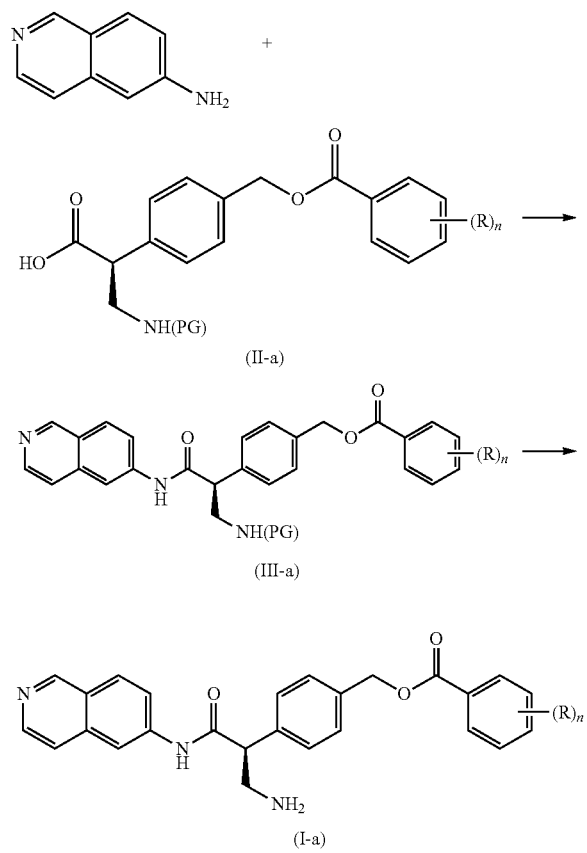

In some embodiments, the synthesis of the compound of formula (II-a) may be provided. Aminoalkylation of the compound of formula (IV-a), wherein T is a chiral auxiliary, can provide the compound of formula (V-a), which can be converted to the compound of formula (II-a) upon removal of the chiral auxiliary.

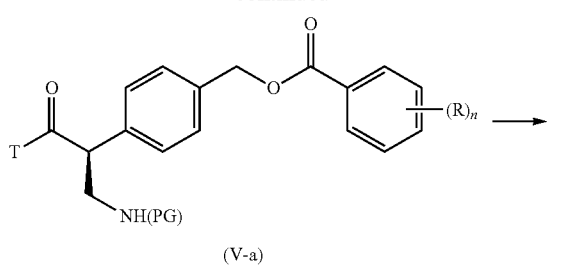

In some embodiments, the synthesis of a compound of formula (VII-a) is provided. The compound of formula (VII-a) can be prepared by reaction of methyl 2-(4-(hydroxymethyl)phenyl)acetate with the compound of formula (VI-a). In some embodiments, the compound of formula (VII-a) can be converted to the compound of formula (VIII-a), wherein $R^1$ is halogen, $OR^a$, $OC(O)R^b$, $SR^a$, or $SC(O)R^b$; wherein $R^a$ is H, alkyl or aryl, and $R^b$ is alkyl or aryl. In some embodiments, the compound of formula (IV-a) can be obtained in turn from the compound of formula (VIII-a), wherein T is a chiral auxiliary.

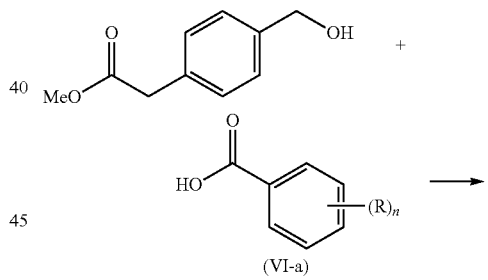

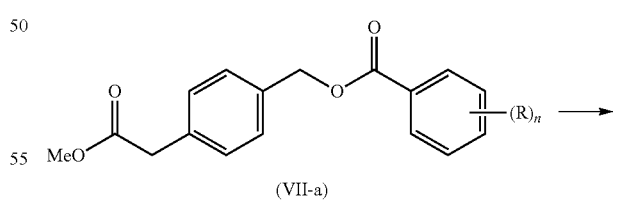

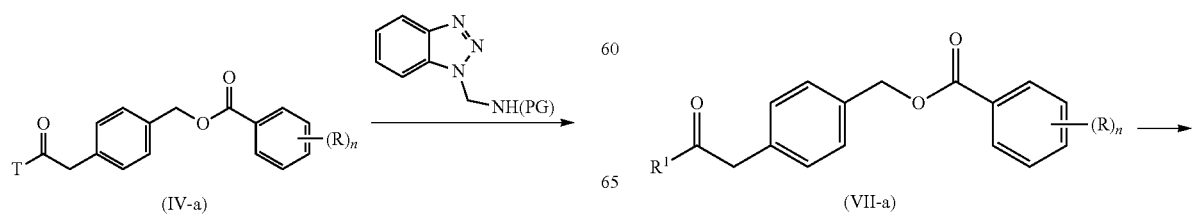

-continued

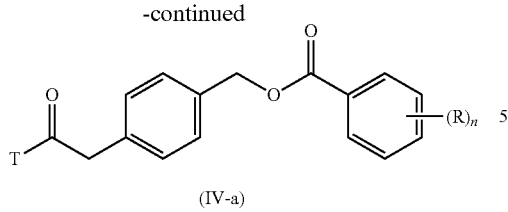

(IV-a)

In certain embodiments, T may be the compound of formula (IX),

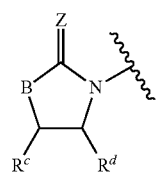

(IX)

wherein Z is S or O; B is S or O; $R^c$ is hydrogen, $C_{1-4}$ alkyl, or aryl; and $R^d$ is $C_1$-$C_4$ alkyl, $C_3$-$C_7$ branched alkyl, arylalkyl or aryl.

Specifically, T may be the compound of formula (IX-a),

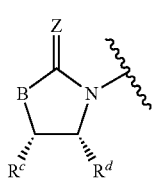

(IX-a)

wherein Z is S or O; B is S or O; $R^c$ is hydrogen or aryl; and $R^d$ is $C_1$-$C_4$ alkyl, arylalkyl or aryl.

More specifically, T may be selected from the group consisting of

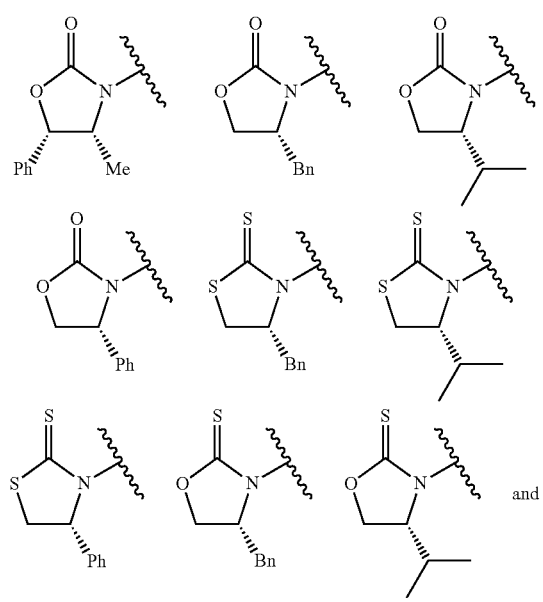

and

-continued

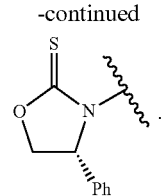

In a specific embodiment, T is

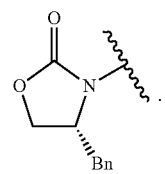 [SMILES: *N1C(=O)OC[C@H]1Cc1ccccc1]

C. Compound (1)

In an embodiment, the disclosed process for the synthesis of the compound of formula (I) may be used to synthesize compound (1):

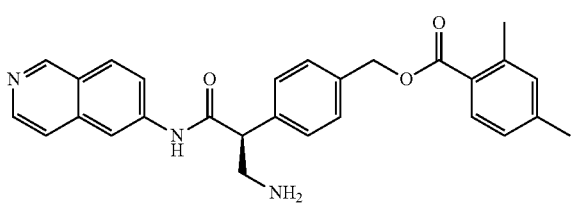

(1)

or a pharmaceutically acceptable salt thereof.

6-Aminoisoquinoline may be reacted with compound (2) to form compound (3). Compound (3) can be transformed to compound (1) by removal of the Boc protecting group.

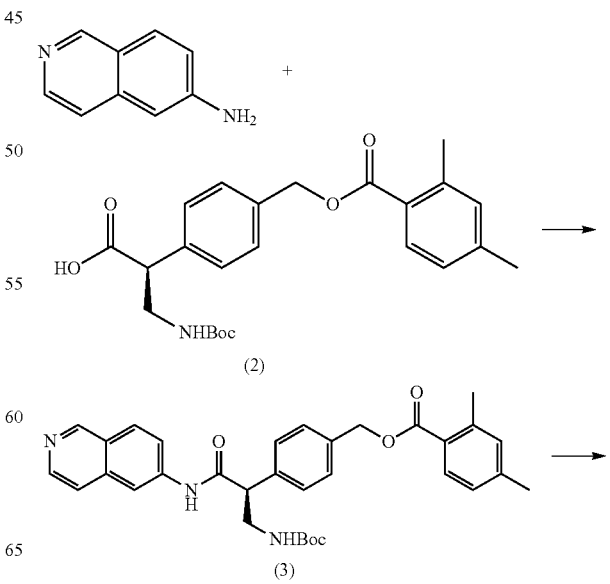

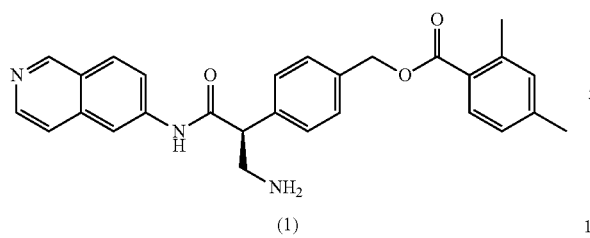

In some embodiment, the synthesis of compound (2) may be included. Aminoalkylation of compound (4) can provide compound (5), which can be converted to compound (2) upon removal of the chiral auxiliary.

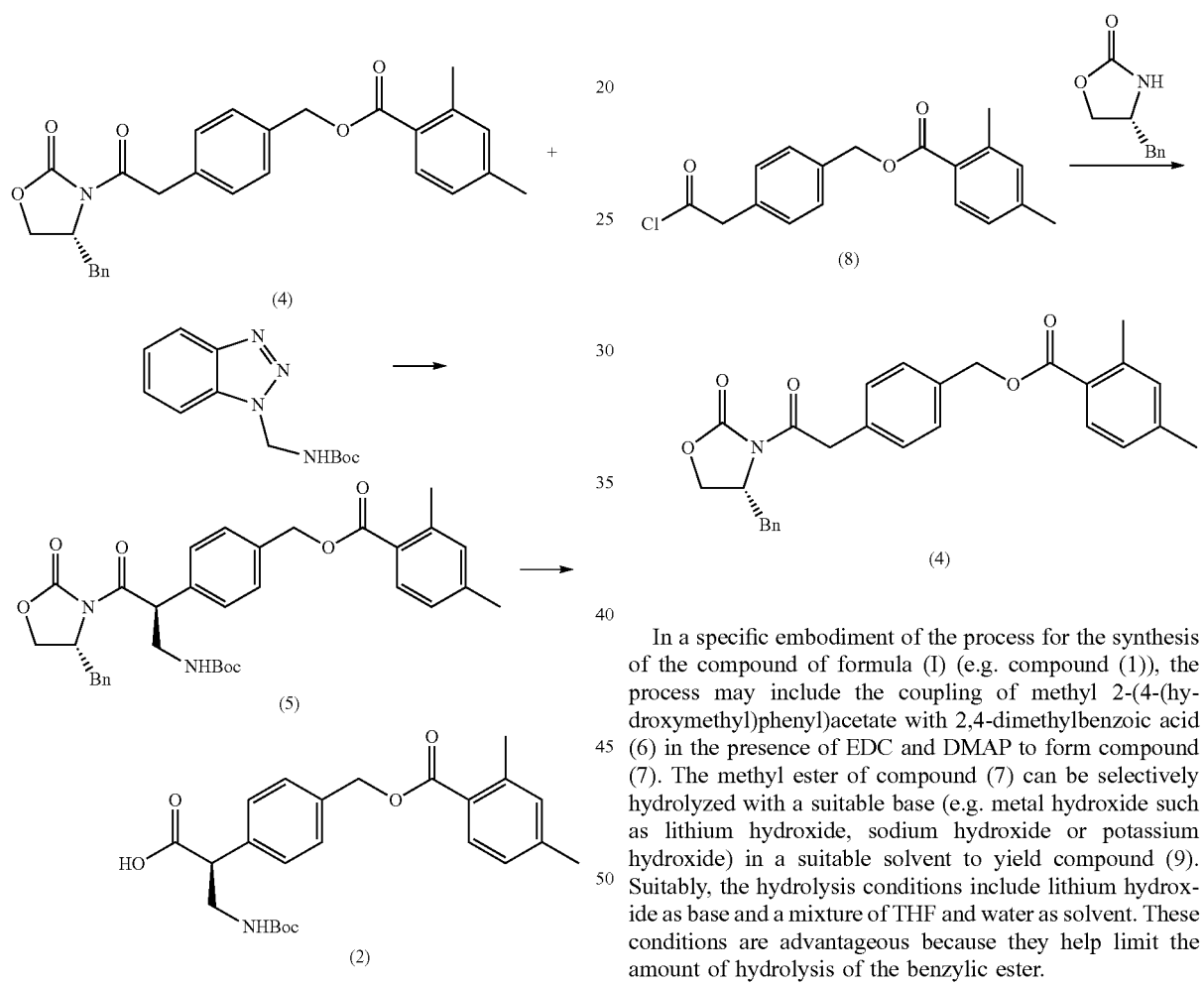

In some embodiments, compound (4) can be prepared by reaction of methyl 2-(4-(hydroxymethyl)phenyl)acetate with compound (6). Compound (7) can be converted to compound (8). Compound (4) can be obtained in turn from compound (8).

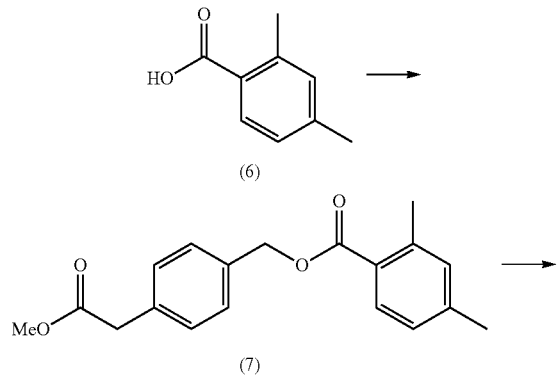

In a specific embodiment of the process for the synthesis of the compound of formula (I) (e.g. compound (1)), the process may include the coupling of methyl 2-(4-(hydroxymethyl)phenyl)acetate with 2,4-dimethylbenzoic acid (6) in the presence of EDC and DMAP to form compound (7). The methyl ester of compound (7) can be selectively hydrolyzed with a suitable base (e.g. metal hydroxide such as lithium hydroxide, sodium hydroxide or potassium hydroxide) in a suitable solvent to yield compound (9). Suitably, the hydrolysis conditions include lithium hydroxide as base and a mixture of THF and water as solvent. These conditions are advantageous because they help limit the amount of hydrolysis of the benzylic ester.

-continued

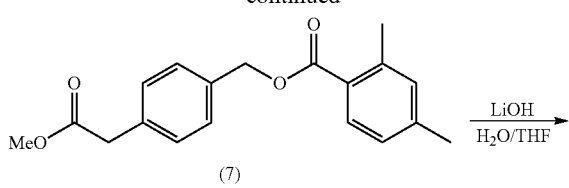

(7)

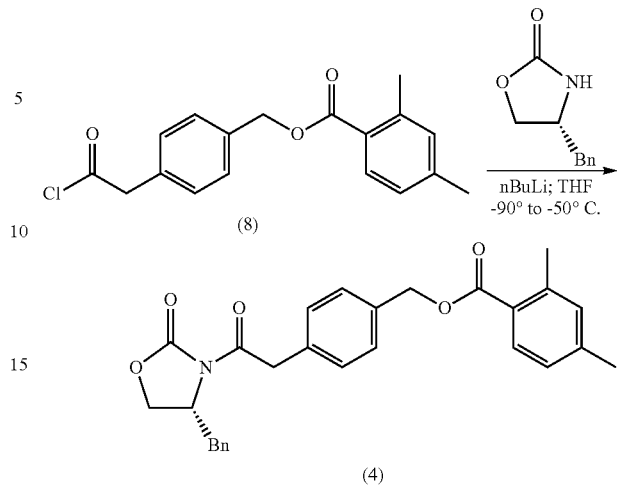

(8)

(4)

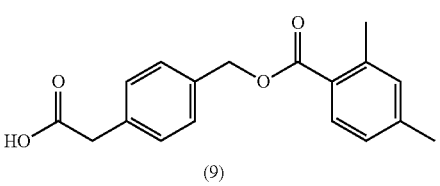

(9)

In some embodiments, compound (9) can be transformed to acid chloride (8) by treatment with a chlorinating agent. The chlorinating agent may be oxalyl chloride or thionyl chloride. The solvent may be a chlorinated solvent such as methylene chloride, dichloroethane or chloroform, or it may be a non-chlorinated solvent such as THF, diethyl ether, dioxane or acetonitrile. The chlorinating agent and solvent may be thionyl chloride. Suitably, the chlorinating agent is oxalyl chloride and the solvent is methylene chloride or a tetrahydofuran/dimethylformamide solvent mixture. Compound (8) may be purified, for example, via recrystallization. Suitable solvents for recrystallization include n-heptane.

In some embodiments, compound (4) can be treated with a base followed by addition of N-Boc-1-aminomethylbenzotriazole at a temperature of −50° C. to −20° C. to provide compound (5) in a diastereoselective fashion. The base used for treatment of compound (4) may be LiHMDS, LDA, or NaHMDS. The solvent may be THF, toluene, diethyl ether, acetonitrile, methyl t-butyl ether or a combination thereof. Suitably, the base used for treatment of compound (4) is LiHMDS and the solvent is THF. In some embodiments, a Lewis acid may be added with the base to facilitate deprotonation of compound (4) to form the reactive intermediate. Compound (5) may be obtained with a diastereomeric ratio of greater than 1:1, greater than 2:1, greater than 5:1, greater than 10:1, greater than 20:1, greater than 50:1 or greater than 99:1. If desired, the minor diastereomer may be removed via standard purification techniques such as, but not limited to, recrystallization and silica gel chromatography.

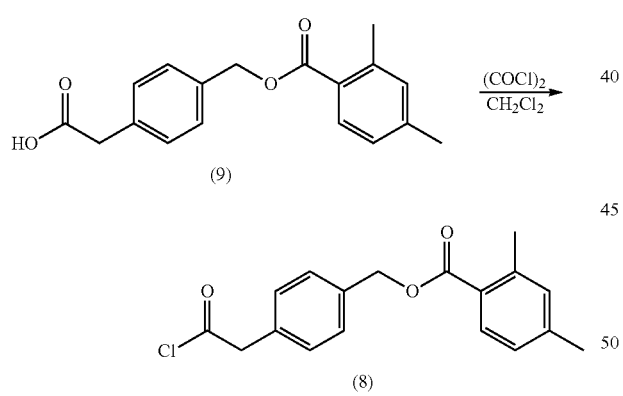

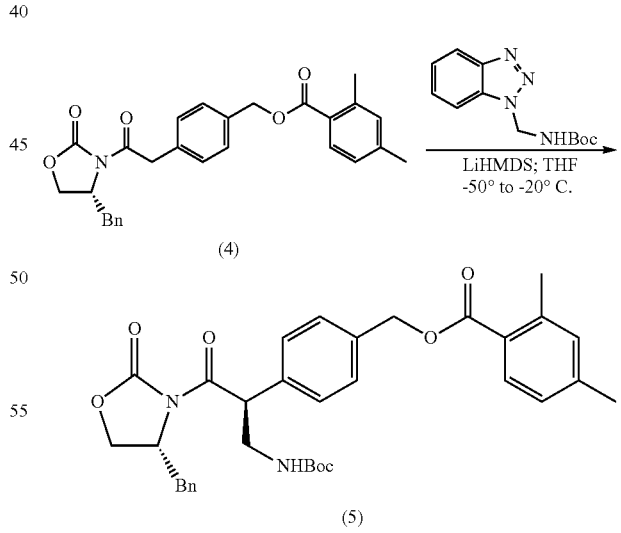

(4)

(5)

In some embodiments, addition of a base to (R)-4-benzyloxazolidin-2-one can be followed by reaction with compound (8) at a temperature of −90° C. to 50° C. to provide compound (4). The base used for addition to (R)-4-benzyloxazolidin-2-one may be NaH, LiH, KH, nBuLi, NaHMDS, LDA, triethylamine, ethyl diisopropylamine, methyl magnesium bromide, sodium carbonate, cesium carbonate, secBuLi, LiHMDS, potassium t-butoxide, sodium isopropoxide or KHMDS. The solvent may be THF, toluene, diethyl ether, acetonitrile, methyl t-butyl ether or a combination thereof. Suitably, the base used for addition to (R)-4-benzyloxazolidin-2-one is nBuLi and the solvent is THF.

In some embodiments, compound (5) can be converted to carboxylic acid (2) by addition of an appropriate nucleophile to remove the oxazolidinone chiral auxiliary. Suitably, the nucleophile is lithium hydroperoxide, which is formed in situ by reaction of lithium hydroxide with hydrogen peroxide. Suitable nucleophiles allow for removing of the chiral auxiliary with minimal or no cleavage of the benzyl ester. Compound (2) may be purified, if desired, for example, by recrystallization.

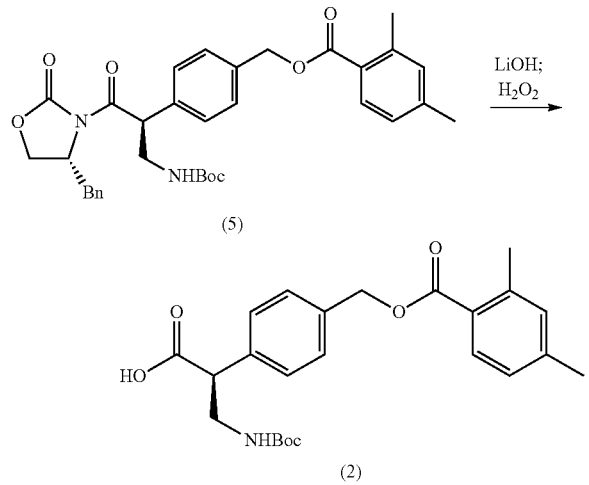

In some embodiments, compound (2) can be converted to compound (3) by activating the carboxylic acid group and reacting with 6-aminoisoquinoline. The carboxylic acid group may be activated by a variety of reagents and conditions, including conversion to a mixed anhydride or acid halide, or use of standard amide coupling reagents (e.g. EDCI, HOBT, DCC, DIC, HBTU, and HATU). Suitably, the carboxylic acid group is activated by formation of a mixed anhydride. In some embodiments, the mixed anhydride can be formed by addition of an alkyl chloroformate such as 1,1-dimethyl-2,2,2-trichloroethyl chloroformate and a base, or by addition of a phosphonic anhydride such as propylphosphonic anhydride and a base.

In one embodiment, phosphonic anhydride and pyridine are added to compound (2) at 0° C. in the presence of 6-aminoisoquinoline. A reactive mixed anhydride intermediate may form under such reaction conditions that may react with 6-aminoisoquinoline to form compound (3).

In a another embodiment, 1,1-dimethyl-2,2,2-trichloroethyl chloroformate and collidine are added to compound (2) at 0° C. in the presence of 6-aminoisoquinoline. In one embodiment, the 1,1-dimethyl-2,2,2-trichloroethyl chloroformate is added to a mixture of compound (2), 6-aminoisoquinoline, and collidine. A reactive mixed anhydride intermediate may form under such reaction conditions that may react with 6-aminoisoquinoline to form compound (3). The solvent employed may be DMF, alone or in combination with methylene chloride, or acetonitrile, and suitably, the solvent employed is DMF. Upon isolation, compound (3) can optionally be purified by silica gel column chromatography and/or recrystallization.

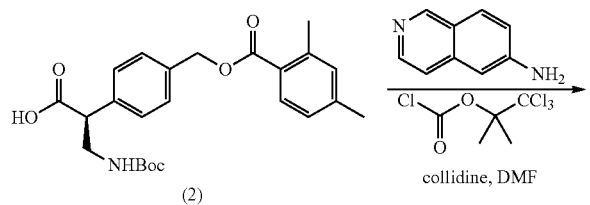

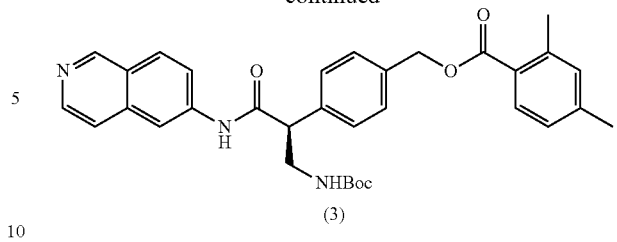

In some embodiments, conversion of compound (3) to compound (1) can be achieved by addition of a suitable reagent to remove the Boc protecting group. Suitably, an acid is used to remove the Boc protecting group. Any acid useful for removing the Boc protecting group may be used. The acid used for removing the Boc protecting group may also promote the formation of a salt of compound (1). The acid may be chosen so as to be advantageous for removal of the protecting group and also form a suitable pharmaceutically acceptable salt. Suitably, the acid employed in the conversion of compound (3) to compound (1) comprises at least two equivalents of methanesulfonic acid, resulting in the dimethanesulfonic acid salt of compound (1). Methanesulfonic acid is particularly useful because the desired product is formed in high yield with few byproducts and little decomposition. The dimethanesulfonic acid salt offers useful properties such as being easily purified, easy to handle and is able to be produced in large scale processes with great reproducibility.

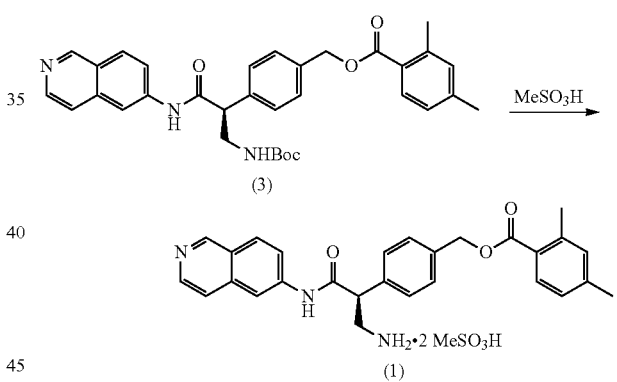

D. Compound of Formula (XI)

In another aspect, disclosed is a process for the synthesis of the compound of formula (XI):

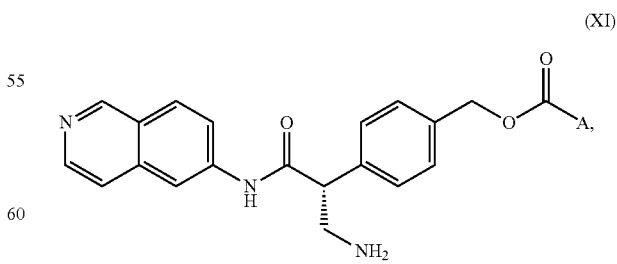

or a pharmaceutically acceptable salt thereof; wherein A is cyclohexyl or phenyl, substituted with 0-3 substituents selected from the group consisting of alkyl, halogen, alkoxy, and cyano.

The process includes reacting 6-aminoisoquinoline with the compound of formula (XII), wherein PG is a protecting group for the nitrogen, to form the compound of formula (XIII). The compound of formula (XIII) can be transformed to the compound of formula (XI) by removal of the nitrogen protecting group. The nitrogen protecting group, PG, may be any suitable nitrogen protecting group known in the art. In certain embodiments, PG is selected from the group consisting of tert-butyloxycarbonyl (Boc), carbobenzyloxy (CBZ), and para-methoxybenzyl carbonyl (Moz).

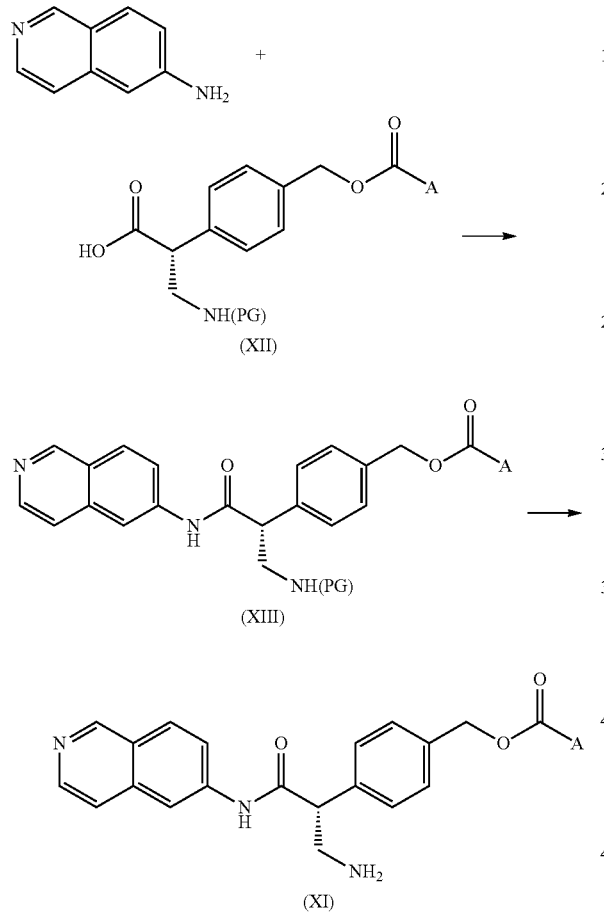

The process further includes the synthesis of the compound of formula (XII). Aminoalkylation of the compound of formula (IV), wherein T is a chiral auxiliary, can provide the compound of formula (XV), which can be converted to the compound of formula (XII) upon removal of the chiral auxiliary.

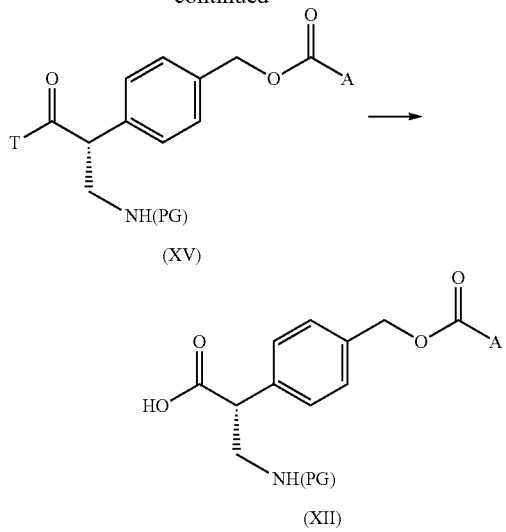

In certain embodiments, the compound of formula (XI) may be obtained via the process described above for the synthesis of the compound of formula (I). In particular, the compound of formula (XV) may be formed in the conversion of the compound of formula (IV) to the compound of formula (V) as a minor product. Employing the reaction steps and schemes described above, the compound of formula (XV) may, in turn, be transformed to the compound of formula (XI). Accordingly, intermediate compounds, the compounds of formulae (XII) and (XIII), may thus also be formed in the process.

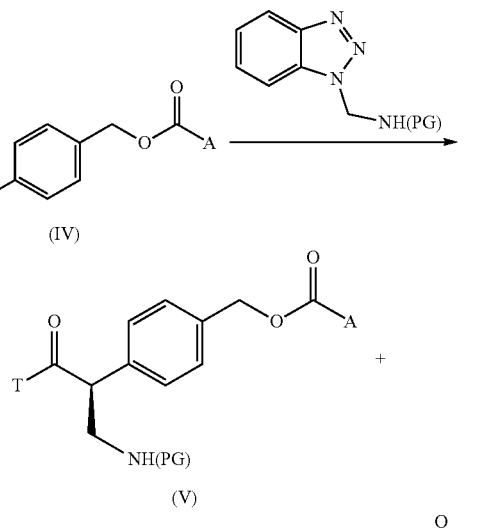

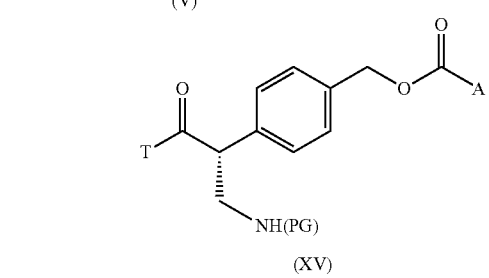

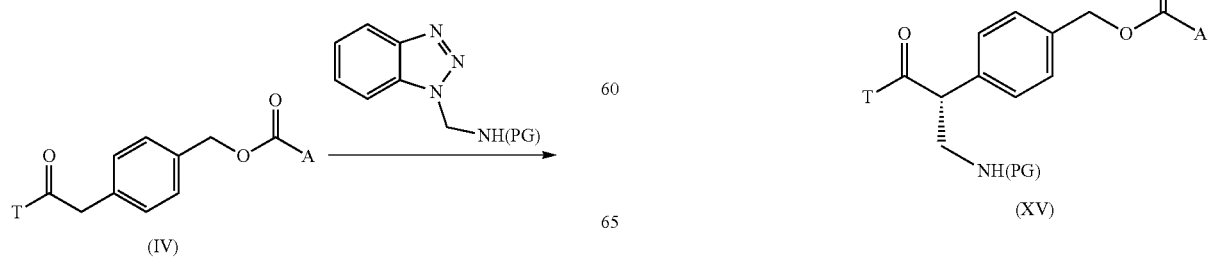

E. Compound of Formula (XI-a)

In an embodiment, the synthesis of the compound of formula (XI-a) is provided:

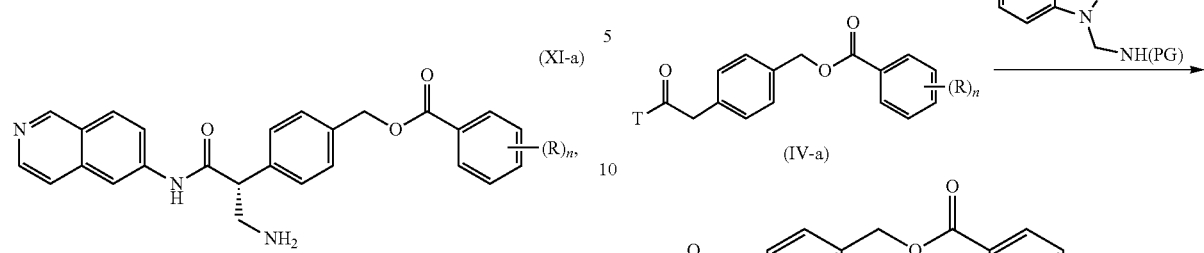

or a pharmaceutically acceptable salt thereof; wherein each R is independently selected from the group consisting of $C_{1-4}$ alkyl, halogen, $C_{1-4}$ alkoxy and cyano; and n is an integer from 0 to 3. In one embodiment, the $C_{1-4}$ alkyl is a $C_{1-4}$ fluoroalkyl.

The process includes reacting 6-aminoisoquinoline with the compound of formula (XII-a), wherein PG is a protecting group for the nitrogen, to form the compound of formula (XIII-a). The compound of formula (XIII-a) can be transformed to the compound of formula (XI-a) by removal of the nitrogen protecting group. The nitrogen protecting group, PG, may be any suitable nitrogen protecting group known in the art. In certain embodiments, PG is selected from the group consisting of tert-butyloxycarbonyl (Boc), carbobenzyloxy (CBZ), and para-methoxybenzyl carbonyl (Moz).

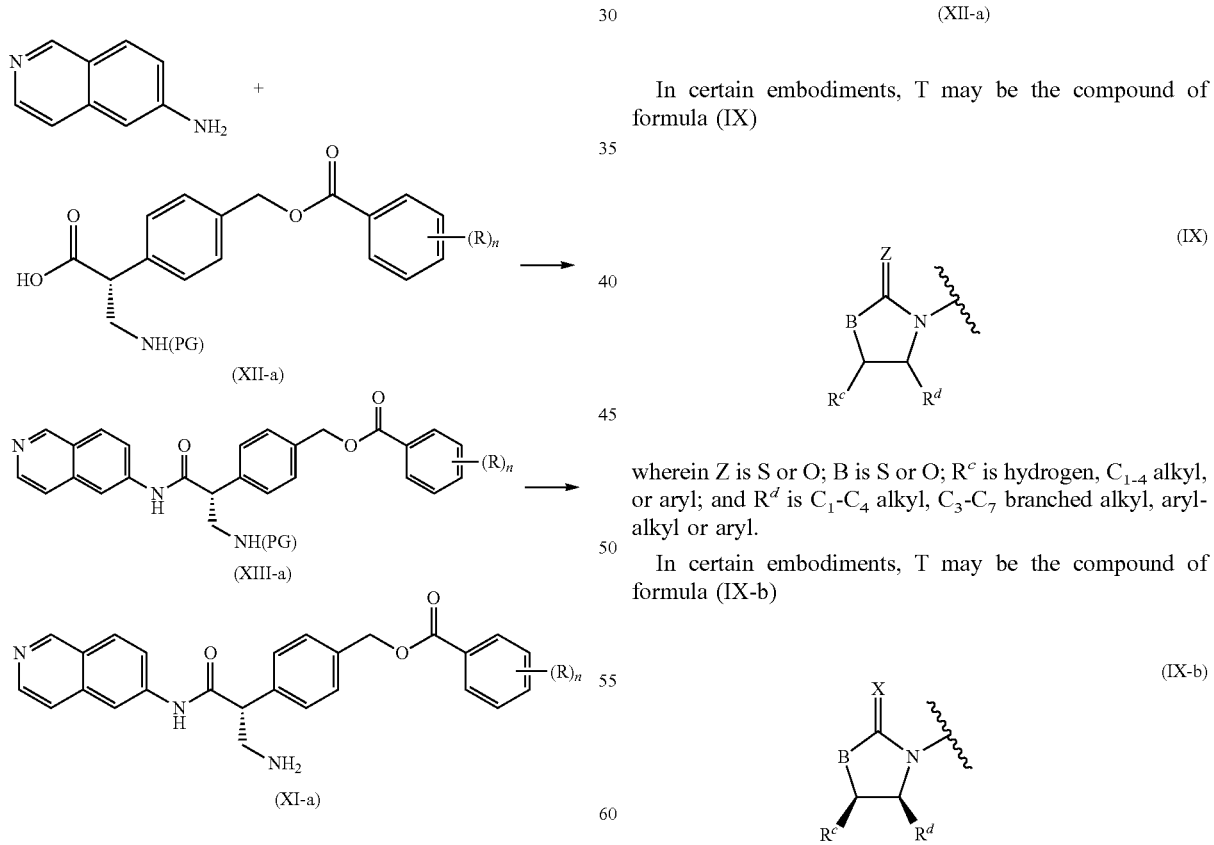

Synthesis of the compound of formula (XII-a) may also be included. Aminoalkylation of the compound of formula (IV-a), wherein T is a chiral auxiliary, can provide the compound of formula (XV-a), which can be converted to the compound of formula (XII-a) upon removal of the chiral auxiliary.

In certain embodiments, T may be the compound of formula (IX)

wherein Z is S or O; B is S or O; $R^c$ is hydrogen, $C_{1-4}$ alkyl, or aryl; and $R^d$ is $C_1$-$C_4$ alkyl, $C_3$-$C_7$ branched alkyl, arylalkyl or aryl.

In certain embodiments, T may be the compound of formula (IX-b)

wherein Z is S or O; B is S or O; $R^c$ is hydrogen or aryl; and $R^d$ is $C_1$-$C_4$ alkyl, arylalkyl or aryl.

In certain embodiments, T may be selected from the group consisting of

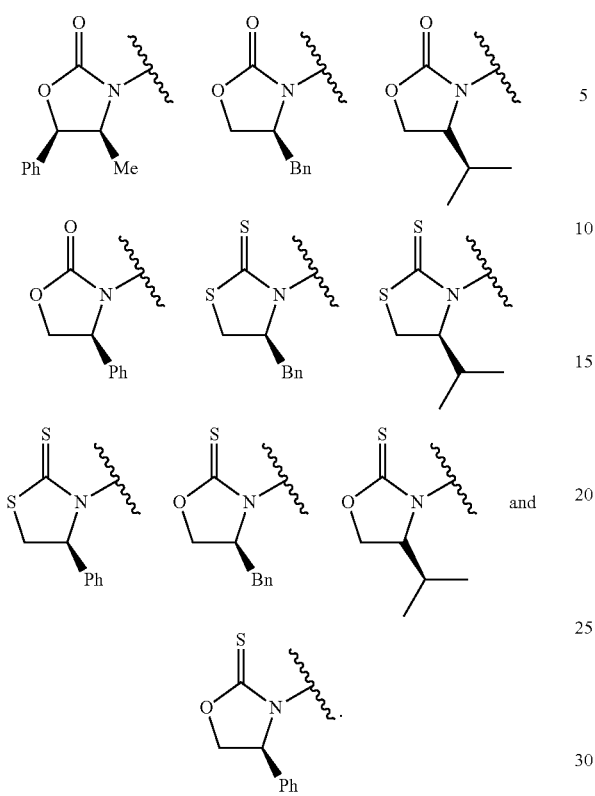

In a specific embodiment, T is

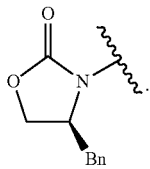 [SMILES: *N1C(=O)OC[C@@H]1Cc1ccccc1]

In certain embodiments, the compound of formula (XI-a) may be obtained via the process described above for the synthesis of the compound of formula (I-a). In particular, the compound of formula (XV-a) may be formed in the conversion of the compound of formula (IV-a) to the compound of formula (V-a) as a minor product. Employing the reaction steps and schemes described above, the compound of formula (XV-a) may, in turn, be transformed to the compound of formula (XI-a). Accordingly, intermediate compounds, the compounds of formulae (XII-a) and (XIII-a), may thus also be formed in the process.

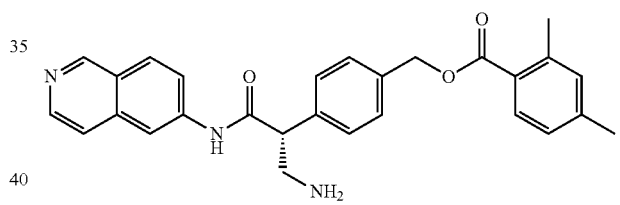

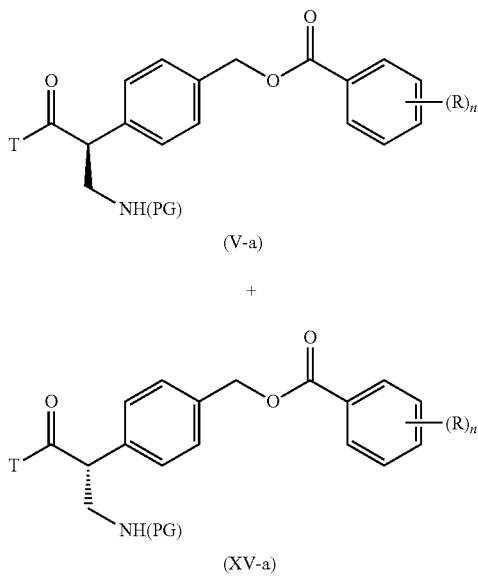

F. Compound (11)

In an embodiment, the process for the synthesis of compound (11) is provided:

(11)

or a pharmaceutically acceptable salt thereof.

The process includes reacting 6-aminoisoquinoline with compound (12) to form compound (13). Compound (13) can be transformed to compound (11) by removal of the Boc protecting group.

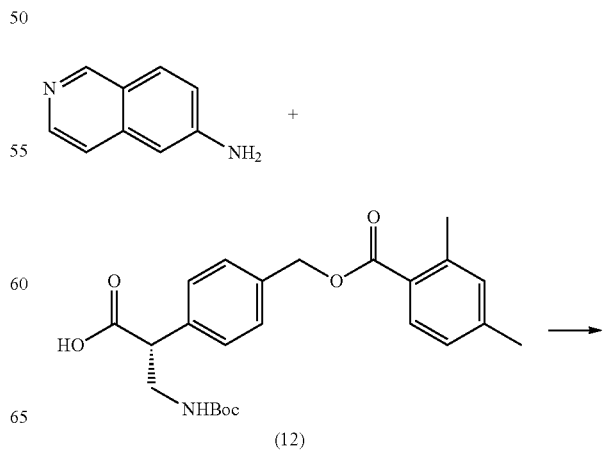

-continued

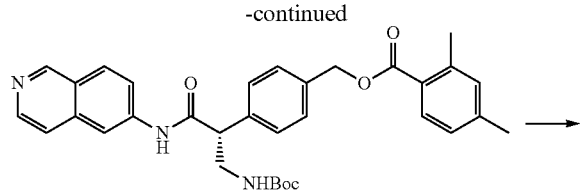

(13)

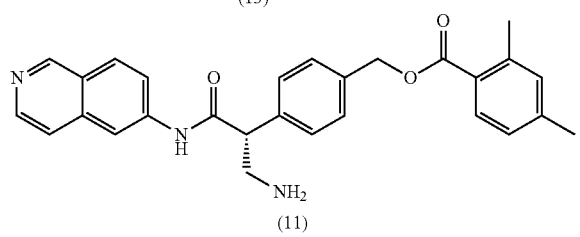

(11)

In some embodiments, the process further includes the synthesis of compound (12). Addition of the chiral auxiliary to compound (8) can afford compound (14). Aminoalkylation of compound (14) can provide compound (15), which can be converted to compound (12) upon removal of the chiral auxiliary.

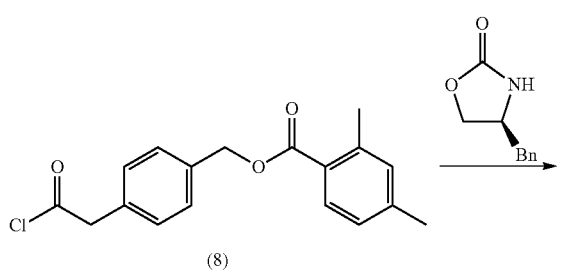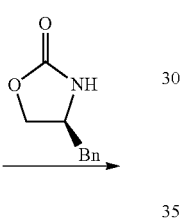

(8)

(14)

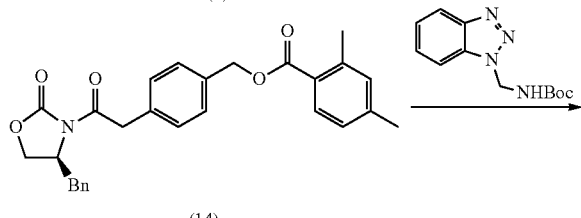

(15)

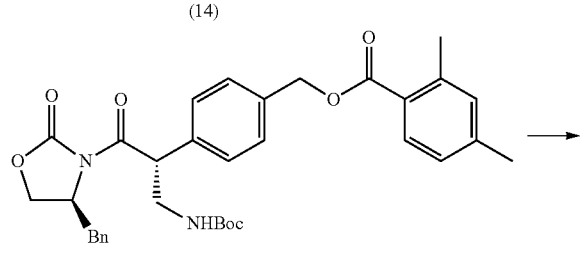

(12)

In certain embodiments, compound (11) may be obtained via the process described above for the synthesis of compound (1). In particular, compound (16) may be formed in the conversion of compound (4) to compound (5) as a minor product. Employing the reaction steps and schemes described above, compound (16) may, in turn, be transformed to compound (11). Accordingly, intermediate compounds, compounds (12) and (13), may thus also be formed in the process.

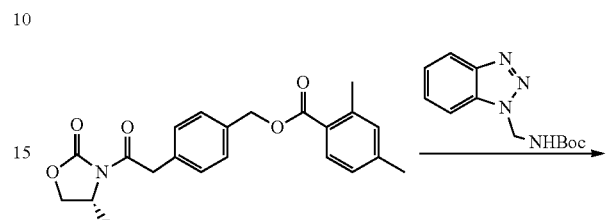

(4)

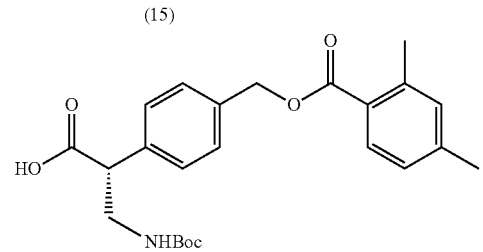

(5)

+

(16)

In another aspect, the invention provides a method for formation of an amide or ester bond comprising reacting an amine or alcohol with a carboxylic acid in the presence of

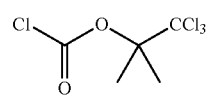

and a base. The amine and ester may be generally thought to be unreactive. In one embodiment, the amine is an aromatic amine. In one embodiment, the alcohol is an aromatic alcohol. The 1,1-dimethyl-2,2,2,-trichloroethyl chloroformate may allow for stereoselective coupling of easily racemized carboxylic acids, particularly alpha-aromatic acids.

In another aspect, the invention provides a method for formation of A method for synthesizing an alpha-alkylated imide comprising reacting an oxazolidinyl imide with

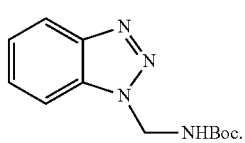 [SMILES: CC(C)(C)OC(=O)NCn1nnc2ccccc21]

Abbreviations which have been used in the descriptions of the above structures and schemes include: Bn for benzyl; Ph for phenyl; Me for methyl; EDC for N-(3-Dimethylaminopropyl)-N'-ethylcarbodiimide hydrochloride; Boc for tert-butyl carbonyl; EDCI for 1-ethyl-3-(3-dimethylaminopropyl)carbodiimide, HOBT for hydroxybenzotriazole, CDI for carbonyl diimidazole; DCC for N,N'-dicyclohexylcarbodiimide; DIC for N,N'-disopropylcarbodiimide, HBTU for 2-(1H-benzotriazol-1-yl)-1,1,3,3-tetramethyluronium hexafluorophosphate; HATU for 1-[bis(dimethylamino) methylene]-1H-1,2,3-triazolo[4,5-b]pyridinium 3-oxid hexafluorophosphate; DMAP for dimethylaminopyridine; LiHMDS for lithium hexamethyldisilazide; NaHMDS for sodium hexamethyldisilazide; KHMDS for potassium hexamethyldisilazide; LDA for lithium diisopropylamide; DMF for dimethylformamide; and THF for tetrahydrofuran.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4th ed.), John Wiley & Sons, NY (2006), which is incorporated herein by reference in its entirety. It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. Compounds

A. Compound of Formula (I)

In another aspect, disclosed herein are compounds of formula (I):

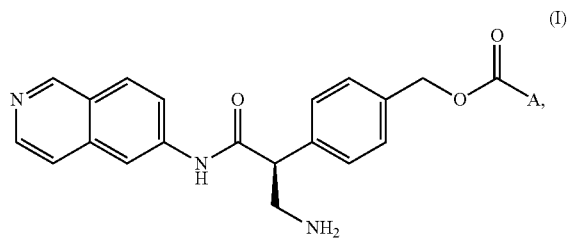

or a pharmaceutically acceptable salt thereof; wherein A is cyclohexyl or phenyl, substituted with 0-3 substituents selected from the group consisting of alkyl, halogen, alkoxy, and cyano.

In an embodiment, the compound of formula (I) is the compound of formula (I-a):

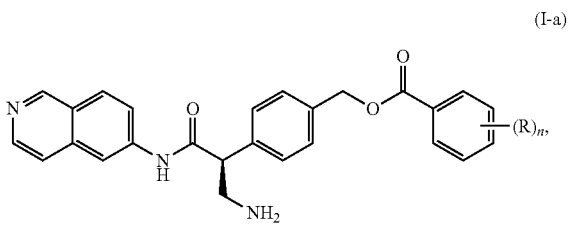

or a pharmaceutically acceptable salt thereof wherein each R is independently selected from the group consisting of $C_1$-$C_4$ alkyl, halogen, $C_1$-$C_4$ alkoxy and cyano; and n is an integer from 0 to 3.

In an embodiment, the compound of formula (I) is compound (1):

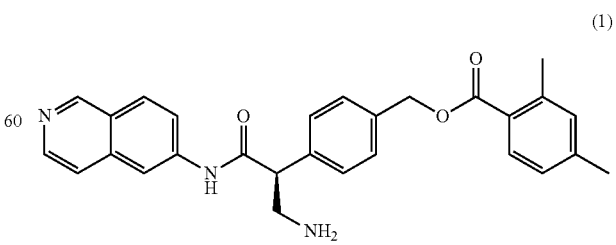

or a pharmaceutically acceptable salt thereof.

In another aspect, disclosed herein are compounds of formula (XI):

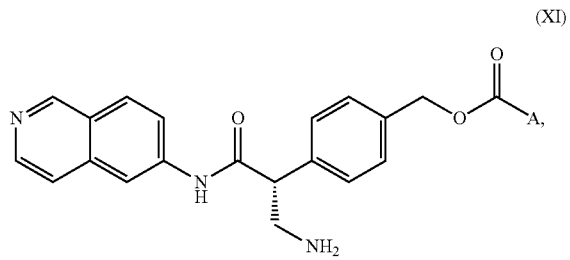

or a pharmaceutically acceptable salt thereof wherein A is cyclohexyl or phenyl, substituted with 0-3 substituents independently selected from the group consisting of alkyl, halogen, alkoxy, and cyano.

In an embodiment, the compound of formula (XI) is the compound of formula (XI-a):

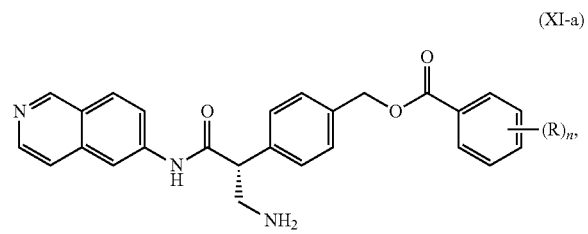

or a pharmaceutically acceptable salt thereof wherein each R is independently selected from the group consisting of $C_1$-$C_4$ alkyl, halogen, $C_1$-$C_4$ alkoxy and cyano; and n is an integer from 0 to 3.

In an embodiment, the compound of formula (XI) is compound (11):

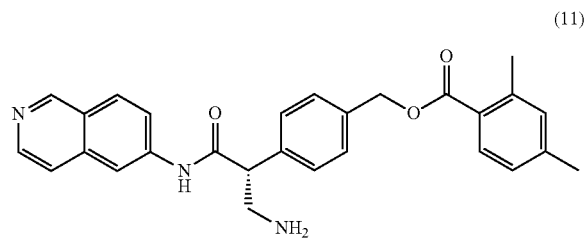 [SMILES: Cc1ccc(C(=O)OCc2ccc([C@H](CN)C(=O)Nc3ccc4cnccc4c3)cc2)c(C)c1]

or a pharmaceutically acceptable salt thereof.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I), but for the fact that one or more atoms are replaced by an atom having an atomic mass or mass number different from the atomic mass or mass number prevalent found in nature. Examples of isotopes suitable for inclusion in the compounds of the invention are isotopes of hydrogen, carbon, nitrogen, oxygen, phosphorus, sulfur, fluorine, and chlorine, such as, but not limited to $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a free carboxyl group, if present in the molecule, with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

The compounds and processes of the invention will be better understood by reference to the following examples, which are intended as an illustration of and not a limitation upon the scope of the invention.

4. Examples

Unless otherwise stated, temperatures are given in degrees Celsius (° C.); synthetic operations were carried out at ambient temperature, "rt," or "RT," (typically a range of from about 18-25° C.); evaporation of solvents was carried out using a rotary evaporator under reduced pressure (typically, 4.5-30 mm Hg) with a bath temperature of up to 60° C.; the course of reactions was typically followed using thin layer chromatography (TLC); all melting points, if given, are uncorrected; all intermediates as well as the final product exhibited satisfactory $^1$H-NMR, HPLC and/or microanalytical data; and the following conventional abbreviations are used: L (liter(s)), mL (milliliters), mmol (millimoles), g (grams), mg (milligrams), min (minutes), and h (hours).

Proton magnetic resonance ($^1$H NMR) spectra were recorded on either a Varian INOVA 600 MHz ($^1$H) NMR spectrometer, Varian NOVA 500 MHz ($^1$H) NMR spectrometer, Varian Mercury 300 MHz ($^1$H) NMR spectrometer, or a Varian Mercury 200 MHz ($^1$H) NMR spectrometer. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz).

Example 1: 2-(4-(((2,4-Dimethylbenzoyl)oxy)methyl)phenyl)acetic acid (9)

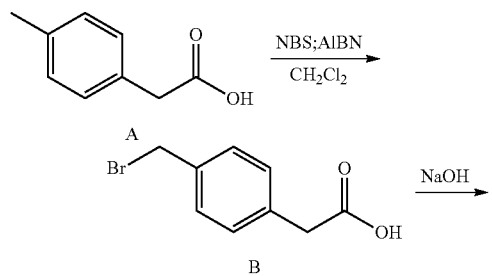

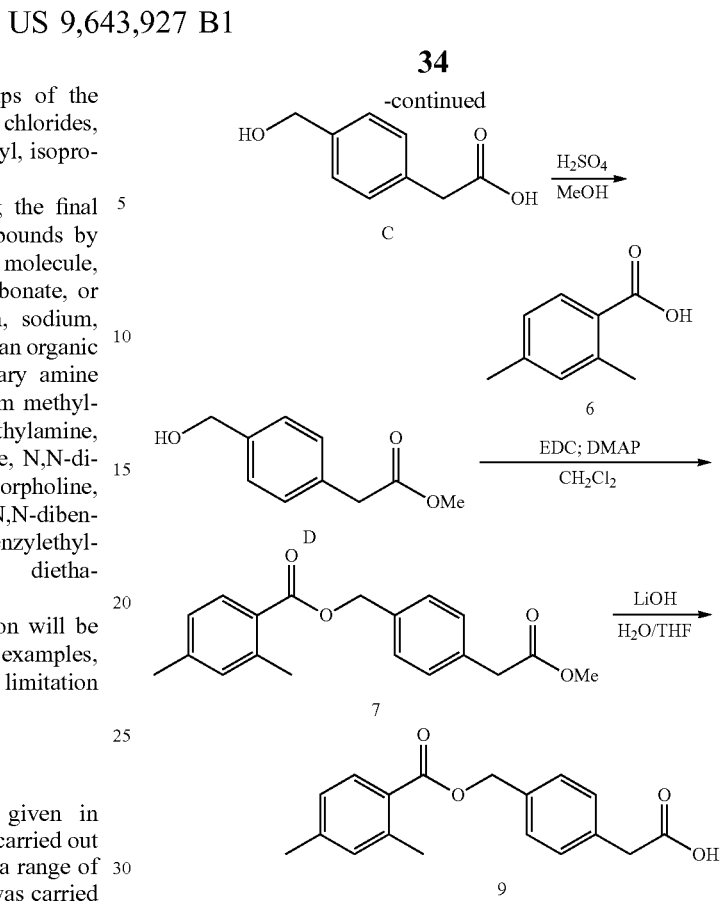

2-(4-(Bromomethyl)phenyl)acetic acid (B)

To a solution of A (4.4 kg, 29.3 mol, 1 eq) in acetonitrile (22 L) was added N-bromosuccinimide (NBS) (5740 g, 32.2 mol, 1.1 eq) and azobisisobutyronitrile (AIBN) (9.2 g, 0.02 eq). The resulting mixture was slowly heated to 80° C. and stirred for 15-30 min. After the starting 1 was consumed as indicated by TLC, the reaction mixture was cooled to −5° C. slowly and kept at −5° C. overnight. The resulting solid was collected by filtration. The filter cake was washed with petroleum ether/EtOAc (1:1) (5 L), petroleum ether (5 L×2), saturated NaHSO3 (aq.) (5 L), water (5 L), and petroleum ether (5 L) to give the title compound (2.3 kg, yield: 34.2%). HPLC purity: 96.8% (254 nm); $^1$H NMR (300 MHz, DMSO-d$_6$) δ 12.3 (s, 1H), 7.4 (d, J=8.0 Hz, 2H), 7.2 (d, J=8.0 Hz, 2H), 4.7 (s, 2H), 3.57 (s, 2H).

2-(4-(Hydroxymethyl)phenyl)acetic acid (C)

To a solution of NaOH (1.61 kg, 40.2 mol, 4 eq) in water (90 L) was added B (2.3 kg, 10.0 mol, 1 eq) and the resulting mixture was stirred at RT overnight. TLC analysis indicated consumption of B. The reaction mixture was then carefully acidified with concentrated H$_2$SO$_4$ (1.0 L) to pH~2. Then, solid NaCl (25 kg) was added to the mixture followed by extraction with EtOAc (33 L×3). The combined organic phase was washed with brine, dried over Na$_2$SO$_4$, and concentrated until a significant amount of solid precipitated. The resulting suspension was kept at ~4-6° C. overnight to allow for further crystallization. The solid product was then collected by filtration. The filter cake was washed with petroleum ether (2 L×2) to yield the title compound (1.2 kg, yield: 71.9%). HPLC purity: 97.8% (220 nm); $^1$H NMR (300

MHz, DMSO-d$_6$) δ 12.27 (s, 1H), 7.26-7.12 (m, 4H), 5.14 (s, 1H), 4.47 (s, 2H), 3.53 (s, 2H).

Methyl 2-(4-(hydroxymethyl)phenyl)acetate (D)

To a solution of C (2.5 kg, 15.06 mol, 1 eq) in MeOH (15 L) was slowly added concentrated H$_2$SO$_4$ (1.5 L) at 0° C. The resulting mixture was allowed to stir at RT overnight. After C was consumed as indicated by TLC, the reaction mixture was poured into water (20 L) and extracted with EtOAc (20 L×3). The combined organic layers were washed with saturated NaHCO$_3$ solution (aq.) (20 L×3) and then brine (20 L). The organic phase was dried over Na$_2$SO$_4$, filtered and concentrated to give the title compound (2.2 kg) as a viscous oil. HPLC purity: 90% (220 nm); $^1$H NMR (300 MHz, CDCl$_3$) δ 7.35-7.28 (m, 4H), 4.68 (s, 2H), 3.70 (s, 3H), 3.64 (s, 2H).

4-(2-Methoxy-2-oxoethyl)benzyl 2,4-dimethylbenzoate (7)

A solution of 2,4-dimethylbenzoic acid (6) (2.01 kg, 13.4 mol, 1.1 eq) and EDC (4.2 kg, 21.9 mol, 1.8 eq) in dichloromethane was stirred at RT for 1 h. D (2.2 kg, 12.2 mol, 1 eq) and 4-dimethylaminopyridine (DMAP) (298 g, 2.44 mol, 0.2 eq) were added to the reaction mixture, which was allowed to stir at RT overnight. After consumption of D was complete as judged by TLC, the reaction mixture was washed three times with 1 N HCl solution (16 L×3), then once with brine (16 L). The separated organic layer was dried over Na$_2$SO$_4$, filtered, and concentrated. The crude product was recrystallized in MeOH to afford the title compound (2.32 kg, yield 60.9%). HPLC purity: 98.6% (210 nm); $^1$H NMR (300 MHz, CDCl$_3$) δ 7.88 (d, J=7.8 Hz, 1H), 7.42 (d, J=8.0 Hz, 2H), 7.31 (d, J=8.0 Hz, 2H), 7.05 (m, 2H), 5.32 (s, 2H), 3.72 (s, 3H), 3.64 (s, 2H), 2.60 (s, 3H), 2.36 (s, 3H).

2-(4-(((2,4-Dimethylbenzoyl)oxy)methyl)phenyl) acetic acid (9)

To a solution of 7 (1.2 kg, 3.85 mol, 1 eq) in THF (2.4 L) was added a solution of LiOH (176 g, 4.2 mol, 1.1 eq) in water (3.6 L) dropwise over 1 h. The resulting mixture was allowed to stir for 1.5 h. TLC analysis indicated the consumption of 7. The reaction mixture was washed with MTBE (2.5 L×4). The aqueous layer was acidified with a saturated citric acid aqueous solution (550 mL) to pH 3-4, which forms a precipitate. The resulting admixture was concentrated by rotary evaporator to remove the organic solvents. The solid product was then collected by filtration. The crude product was slurried in water (3.5 L) for 30 min. After filtration, the collected solid was then slurried in heptane (5 L) to produce the title compound (2.05 kg, yield: 89.6%). HPLC purity: 100% (210 nm); LCMS (ESI-): m/z=297 (M-1). 1H NMR (300 MHz, CDCl$_3$) δ 7.88 (d, J=7.8 Hz, 1H), 7.43 (d, J=8.0 Hz, 2H), 7.32 (d, J=8.0 Hz, 2H), 7.05 (m, 2H), 5.32 (s, 2H), 3.69 (s, 2H), 2.59 (s, 3H), 2.36 (s, 3H). The compound may be recrystallized from water/acetone if the analytical data indicate the presence of residual citric acid.

Example 2: 4-(2-chloro-2-oxoethyl)benzyl 2,4-dimethylbenzoate (8)

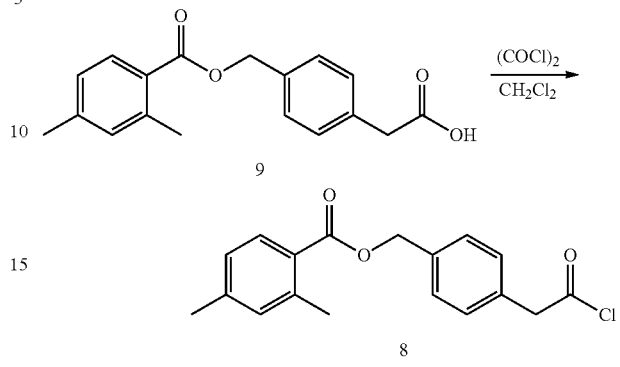

4-(2-chloro-2-oxoethyl)benzyl 2,4-dimethylbenzoate (8)

To a reactor was added 9 (750.19 g) and oxalyl chloride (1.15 equivalents) in dichloromethane, followed by stirring for 18 h at RT. (The disappearance of 9 was monitored by TLC after treatment of a 0.5 ml reaction aliquot with methanol (1 ml). The title compound (8) was quantitatively transformed into the corresponding methyl ester (compound 7) in the presence of an excess of methanol. The TLC results were confirmed by comparison of a $^1$H NMR spectrum of the starting material 9 versus the spectrum of an evaporated aliquot of the reaction mixture.) The reaction mixture was transferred to a rotary evaporator, concentrated to an oil, chase distilled with dichloromethane, and dried overnight to afford 794.7 g (98.8% yield) of the title compound as a white solid. Since 8 is reactive and cannot be chromatographed, characterization by IR and comparison to a reference spectrum was carried out to confirm identification of the compound.

Example 3: (R)-4-(2-(4-benzyl-2-oxooxazolidin-3-yl)-2-oxoethyl)benzyl 2,4-dimethylbenzoate (4)

(R)-4-(2-(4-benzyl-2-oxooxazolidin-3-yl)-2-oxo-ethyl)benzyl 2,4-dimethylbenzoate (4)

A solution of (R)-(+)-4-benzyl-2-oxazolidinone (0.95 equiv.) in THF was treated with n-butyllithium in heptane (1.05 equiv.) at −70° C., followed by addition of a solution of 8 (794.6 g, 1.0 equiv.) in THF at a rate to maintain the internal temperature below −65° C. After stirring for thirty minutes, TLC indicated complete conversion and the reaction was quenched with 10% NH$_4$C$_1$ (aq.). Removal of the aqueous layer was followed by concentration of the organic layer to remove the THF. The resulting residue was dissolved in ethyl acetate. After water and brine washes, the resulting organic extract was concentrated in vacuo. The residue was then chase distilled with dichloromethane to afford 1136.5 g of crude product.

The resulting crude product was diluted with dichloromethane to give a 43.4% w/w solution that was divided into two portions for silica gel chromatography. The splitting of the 43.4% w/w dichloromethane solution maintained a 6.5:1 ratio of silica gel to crude product found to be useful for successful purification. The two portions of 43.4% w/w dichloromethane solution contained 552.4 g and 568.4 g of crude material respectively. Both dichloromethane portions were then further diluted with enough heptane/MTBE (3:1) mixture to make each portion a solution in heptane/dichloromethane/MTBE (3:2:1) solvent mixture. Each purification was achieved with a 5 kg silica gel column, and eluted with 60 L of heptane/MTBE (75:25), followed by heptane/ethyl acetate (3:1) until the desired product had eluted. Fractions containing a high concentration of the desired material, irrespective of the impurities content, were pooled and concentrated in vacuo to afford 937.2 g of solid material.

The residue was then dissolved in 3 volumes of ethyl acetate. A polish filtration was performed using a 20 μm Nylon filter and rinsing with 0.5 volumes of ethyl acetate. The solution was treated with heptane (7 volumes) resulting in the formation of a solid upon stirring overnight. The mixture was cooled to 5° C. and filtered. The solid product was isolated via filtration. The resulting solid was washed with additional heptane followed by drying in an oven under vacuum to afford the title compound as a white solid (707.2 g; 63.6% assay-corrected yield). The use of multiple glass drying dishes (as appropriate to scale) was determined to be beneficial for drying of the solid. $^1$H NMR (500 MHz, CDCl$_3$) δ: 2.35 (s, 3H), 2.59 (s, 3H), 2.77 (dd, J=9.4, 13.4 Hz, 1H), 3.27 (dd, J=3.1, 13.3 Hz, 1H), 4.19 (m, 2H), 4.33 (dd, J=15.6, 36.9 Hz, 2H), 4.69 (m, 1H), 5.33 (s, 2H), 7.03 (d, J=8.2H, 1H), 7.06 (s, 1H), 7.14 (d, J=6.9 Hz, 2H), 7.28 (m, 3H), 7.36 (d, J=8.1 Hz, 2H), 7.44 (d, J=8.1 Hz, 2H), 7.88 (d, J=7.9 Hz, 1H). $^{13}$C NMR (125 MHz, CDCl$_3$) δ 21.4, 21.8, 37.7, 41.3, 55.3, 65.9, 66.2, 126.4, 126.4, 127.3, 128.4, 128.9, 129.4, 129.9, 130.9, 132.5, 133.4, 135.1, 135.6, 140.5, 142.6, 153.4, 167.1, 171.2. LC-MS (ES+): m/z=480 (M+23).

Example 4: 4-((S)-1-((R)-4-benzyl-2-oxooxazolidin-3-yl)-3-((tert-butoxycarbonyl)amino)-1-oxopropan-2-yl)benzyl 2,4-dimethylbenzoate (5)

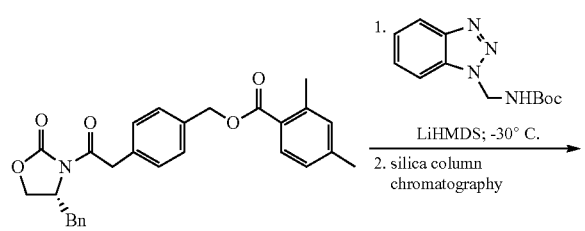

4-((S)-1-((R)-4-benzyl-2-oxooxazolidin-3-yl)-3-((tert-butoxycarbonyl)amino)-1-oxopropan-2-yl)benzyl 2,4-dimethylbenzoate (5)

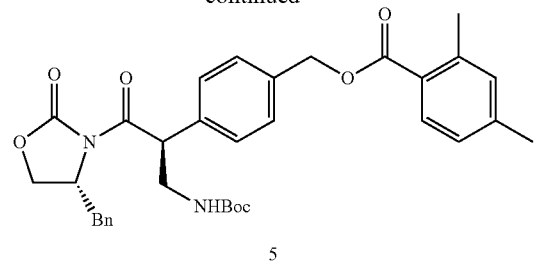

A solution of 4 (691.33 g assay-corrected, 1.0 equiv.) in THF was treated with a solution of LiHMDS in heptane (1.2 equiv. plus adjustments for moisture contained in starting material) at −65° C. to −70° C., followed by stirring for 40 minutes. Addition of a THF solution of N-Boc-1-aminomethylbenzotriazole (1.2 equiv.) was followed by warming to −30° C. and allowed to stir at −30° C. for 90 minutes. The reaction was deemed complete when no further conversion was detected by TLC between samples taken one hour apart. The reaction was quenched by the addition of 2 volumes of 10% NH$_4$Cl (aq.) followed by 2 volumes of 10% citric acid (aq.). The reaction mixture was concentrated to remove a majority of the THF and the resulting mixture was extracted with ethyl acetate. After an aqueous sodium chloride wash, the resulting organic extracts were concentrated in vacuo to afford 1196.9 g of crude product.

The resulting crude product was diluted to give a 23.3% w/w solution in dichloromethane, which was divided into five equivalent portions for silica gel chromatography using pure dichloromethane. The splitting of the 23.3% w/w dichloromethane solution maintained a 20:1 ratio of silica gel to crude product found to be useful for a successful purification. The five columns were loaded with an amount of the 23.3% w/w dichloromethane solution representing 239.7 g, 240.3 g, 236.4 g, 233.8 g, and 229.1 g respectively of crude material. Combining and concentrating the product containing fractions from all five columns followed by drying under high vacuum led to isolation of the title compound as a light yellow solid (619.3 g; 68% assay-corrected yield). $^1$H NMR (500 MHz, CDCl$_3$) δ 1.44 (s, 9H), 2.36 (s, 3H), 2.59 (s, 3H), 2.86 (m, 1H), 3.33 (m, 1H), 3.56 (m, 1H), 3.76 (m, 1H), 4.09 (m, 2H), 4.64 (m, 1H), 4.84 (m, 1H), 5.21 (m, 1H), 5.29 (s, 2H), 7.04 (d, J=8.2 Hz, 1H), 7.06 (s, 1H), 7.23 (d, J=7.2 Hz, 2H), 7.30 (m, 1H), 7.36 (m, 6H), 7.87 (d, J=7.9 Hz, 1H). 13C NMR (125 MHz, CDCl3) 21.4, 21.8, 28.3, 37.9, 43.8, 49.8, 55.6, 65.7, 65.9, 79.5, 126.3, 126.4, 127.4, 128.5, 128.9, 128.9, 129.4, 130.8, 132.5, 135.1, 135.6, 135.9, 140.6, 142.7, 152.4, 155.6, 167.1, 172.6. LC-MS (ES+): m/z=609.2 (M+23)

Example 5: (S)-3-((tert-Butoxycarbonyl)amino)-2-(4-(((2,4-dimethylbenzoyl)oxy)methyl)phenyl)propanoic acid (2)

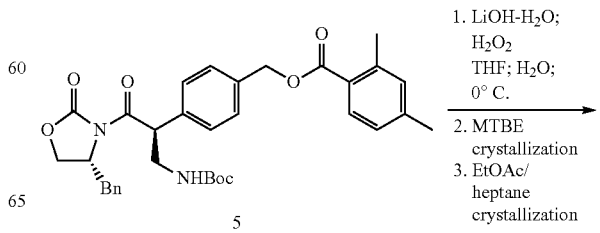

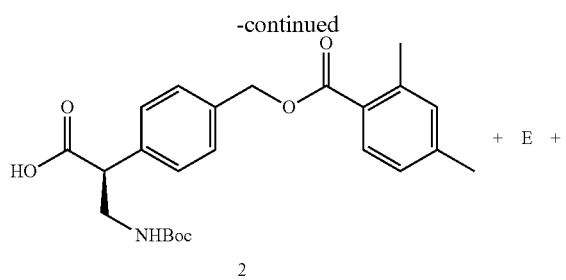

+ E +

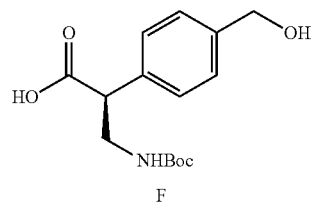

F (S)-3-((tert-Butoxycarbonyl)amino)-2-(4-(((2,4-dimethylbenzoyl)oxy)methyl)phenyl)propanoic acid (2)

5 (600.1 g, 1.0 equiv.) was dissolved in a THF/water (75:25) mixture and cooled to −5° C. Treatment of the mixture with $H_2O_2$ (4.0 equiv.), followed by $LiOH.H_2O$ (1.2 equiv.) led to rapid conversion to the peracid intermediate. The reaction mixture was then quenched with aqueous potassium sulfite (6 equiv.). The byproduct sulfate salts were removed by filtration, followed by splitting of the resulting filtrate into two equal portions. The filtrate was concentrated under vacuum to remove the majority of the THF solvent. The two resulting aqueous solutions were combined and extracted with MTBE/citric acid. The organic extracts were washed with water and concentrated.

The resulting residue was dissolved in 4 volumes of MTBE. Upon seeding with (R)-(+)-4-benzyl-2-oxazolidinone and cooling to −25° C., a solid crystallized out. Compound E was removed by filtration, the filtrates were condensed, and the resulting residue was chase distilled twice with ethyl acetate and dried under high vacuum.

Crystallization of the resulting solid was performed using 4 volumes of ethyl acetate based upon the weight of the dried residue and 14 volumes of heptane as the anti-solvent. Upon stirring overnight, a white solid crystallized out which was filtered and dried to obtain 371.7 g of the title compound, which was subjected to in-process purity and chiral purity analyses. The solid met all preestablished specifications for these two tests except for the levels of compound E and (S)-3-((tert-butoxycarbonyl)amino)-2-(4-(hydroxymethyl)phenyl)propanoic acid (F), both byproducts of the reaction.

Additional recrystallization of the solid was accomplished using 4 volumes of ethyl acetate based upon the weight of the solid and 14 volumes of heptane as the anti-solvent. After drying under high vacuum, the title compound was produced as a white solid (341.3 g; 78.0% assay corrected). $^1$HNMR (500 MHz, $CDCl_3$) δ 1.45 (s, 9H), 2.36 (s, 3H), 2.59 (s, 3H), 3.55 (m, 2H), 3.88 (m, 1H), 5.00 (bs, 1H), 5.31 (s, 2H), 7.04 (d, J=8.4 Hz, 1H), 7.07 (s, 1H), 7.31 (d, J=8.0 Hz, 2H), 7.43 (d, J=8.0 Hz, 2H), 7.88 (d, J=7.9 Hz, 1H). 13C NMR (125 MHz, $CDCl_3$) δ 21.4, 21.8, 28.3, 44.6, 52.3, 65.8, 81.5, 126.3, 126.4. 127.9, 128.7, 130.9, 132.5, 135.7, 136.0, 140.6, 142.7, 158.1, 167.2, 176.1. LC-MS (ES+): m/z=450 (M+23).

To reduce the amount of unwanted byproduct F, it may be useful to store the basic, mostly aqueous solution obtained at the end of the first THF evaporation at 5±3° C. in the reactor while the subsequent portion is being evaporated. It may also be useful to neutralize the hydroxide generated after the potassium sulfite addition, to prevent the formation of F.

Example 6: (S)-4-(3-((tert-butoxycarbonyl)amino)-1-(isoquinolin-6-ylamino)-1-oxopropan-2-yl)benzyl 2,4-dimethylbenzoate (3)

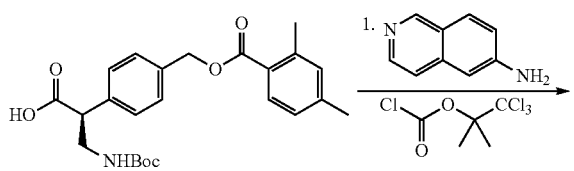

collidine, DMF
2. Silica plug
3. MeCN crystallization
4. $CH_2Cl_2$/heptane crystallization

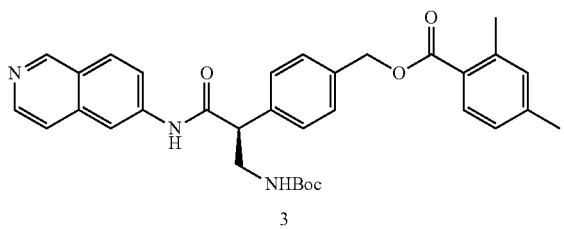

(S)-4-(3-((tert-butoxycarbonyl)amino)-1-(isoquinolin-6-ylamino)-1-oxopropan-2-yl)benzyl 2,4-dimethylbenzoate (3)

A mixture of 2 (340.41 g assay-corrected, 1.0 equiv.), collidine (1.3 equiv.) and 6-aminoisoquinoline (1.3 equiv.) in DMF at 0° C. in a 50 L reactor was treated rapidly with a solution of 2,2,2-trichloro-1,1-dimethylethyl chloroformate (1.3 equiv.) in DMF in a single portion. The reaction was exothermic, with a rise in temperature to about 10° C. Upon stirring for a minimum of 60 minutes, the reaction was assayed by TLC and deemed complete when two samples taken one hour apart showed no further conversion. The reaction was quenched by the addition of 10% $KHCO_3$ (aq.), followed by diluting with ethyl acetate, washing with citric acid, a final 10% $KHCO_3$ (aq.) wash and concentrating to near dryness to afford a crude residue.

The crude residue was dissolved in dichloromethane/ethyl acetate (1:1) and the resulting solution returned to the 50 L reactor, where it was stirred for 4.5 h. The resulting solution was filtered through a 10 μm Teflon filter to remove a colloidal solid. The selection of a 10 μm Teflon filter was based on the filter having enough surface area and being chemically compatible with the dichloromethane/ethyl acetate (1:1) solvent mixture. Concentration of the filtrate in vacuo yielded 666.3 g of crude material.

The resulting crude product was diluted with dichloromethane to give a solution that was divided into two portions for silica gel chromatography. The splitting of the dichloromethane solution maintained a 25:1 ratio of silica gel to crude product found to be useful for successful purification. The two portions of dichloromethane solution represented 166.5 g and 170.2 g of the crude product respectively. The purifications were achieved through the use of two 5 kg silica gel columns eluting with ethyl acetate/heptane (60:40) until the desired product had eluted. Fractions containing a high concentration of the desired material, irrespective of the impurities content, were combined and concentrated to afford 363.3 g of an off-white solid.

The off-white solid was dissolved in dichloromethane and filtered through a 10 μm Teflon filter. The bulk of the solvent was then distilled off and the remainder gradually switched to acetonitrile via chase distillation. At this point, a white solid crystallized and the mixture was cooled to 0±5° C. The solid was isolated by filtration and dried to obtain 333.7 g of a white solid. A sample of the solid was subjected to TLC and HPLC purity analyses. No impurities could be detected by TLC, but the HPLC analysis showed the presence of an unspecified impurity at a level of 0.46% while all identified impurities were below In-Process Action Levels.

A first recrystallization from dichloromethane/heptane was then implemented. After dissolving the solid in dichloromethane, heptane was added and the resulting mixture stirred for 4 h at room temperature. A white solid crystallized out. The solid was filtered and dried to obtain 307.0 g of the solid. A sample of the solid was taken and subjected to TLC and HPLC purity analyses. No impurities could be detected by TLC, but the HPLC analysis showed the presence of the same unspecified impurity, but was reduced to a level of 0.28%.

A second recrystallization was employed. After dissolving the solid in dichloromethane, heptane was added and the resulting mixture stirred for 3.5 h at room temperature. A white solid crystallized out. The solid was filtered and dried to obtain 288.5 g of the solid, which was subjected to HPLC purity analysis. Again, the HPLC analysis showed the presence of the same unspecified impurity, this time reduced to a level of 0.16%.

A third recrystallization was implemented similarly to the first two. After dissolving the solid in dichloromethane, heptane was added and the resulting mixture stirred for 4 h at room temperature. A white solid crystallized out. The white solid was filtered and dried to obtain the title compound as a white solid (272.1 g; 60.5% assay-corrected yield).

A fourth recrystallization from dichloromethane/heptane was utilized. After dissolving the solid in dichloromethane, heptane was added and the resulting mixture stirred for 4 h at room temperature during which time a white solid crystallized out. The white solid was filtered, dried, and subjected to HPLC purity testing. The impurity was detected at less than 0.05%. The fourth recrystallization from dichloromethane/heptane yielded 250.9 g (55.3% assay corrected yield) of the title compound as a white solid.

To achieve even higher purities of the desired product, it may be useful to implement additional recrystallizations. $^1$H NMR (500 MHz, d$_6$-DMSO) δ 1.32 (s, 9H), 2.29 (s, 3H), 2.49 (s, 3H), 3.3 (m, 1H), 3.56 (m, 1H), 4.11 (m, 1H), 5.25 (s, 2H), 7.02 (bt, J=5.4 Hz, 1H), 7.07 (d, J=8.4H, 1H), 7.11 (s, 1H), 7.43 (s, 4H), 7.68 (m, 2H), 7.75 (d, J=7.9 Hz, 1H), 8.02 (d, J=8.7 Hz, 1H), 8.38 (s, 1H), 8.39 (d, J=5.7 Hz, 1H), 9.14 (s, 1H). 13C NMR (125 MHz, d$_6$-DMSO) δ 20.8, 21.2, 28.2, 42.9, 51.7, 65.6, 77.8, 113.1, 120.0, 121.0, 125.0, 126.1, 126.6, 128.0, 128.1, 128.5, 130.4, 132.3, 135.2, 136.1, 137.8, 139.5, 140.4, 142.4, 143.2, 151.5, 155.8, 166.4, 171.0. LC-MS (ES+): m/z=554 (M+1), 576 (M+23).

Example 7: (S)-4-(3-Amino-1-(isoquinolin-6-ylamino)-1-oxopropan-2-yl)benzyl 2,4-dimethylbenzoate dimethanesulfonate (1)

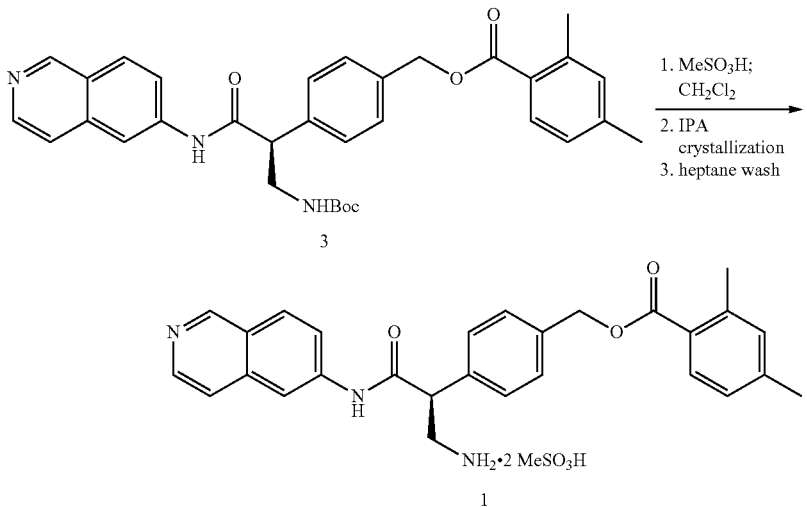

(S)-4-(3-amino-1-(isoquinolin-6-ylamino)-1-oxopropan-2-yl)benzyl 2,4-dimethylbenzoate dimethanesulfonate (1)

A solution of 3 (242.68 g assay-corrected, 1.0 equiv.) in dichloromethane was treated with methanesulfonic acid (2.5 equiv.) and allowed to stir for 48 h at room temperature. The reaction mixture was then heated to reflux for 2 h. Completion of the reaction was ascertained by TLC assay. A gradual solvent switch from dichloromethane to isopropanol was then carried out. The bulk of the dichloromethane solvent was removed by distillation at 45° C. under low vacuum (200-400 mm Hg). Addition of isopropanol, followed by low vacuum distilling at 60° C. until 10 volumes of distillate had been collected led to the removal of residual dichloromethane. A second portion of IPA was added and the volume adjusted by low vacuum distilling at 60° C. to the initial volume of the reaction mixture.

Upon cooling to 20±5° C. and stirring for 9 h at this temperature, the dimesylate salt was isolated as a solid by filtration on a 30 micron Teflon filter housed in a filtration reactor under mechanical stirring and a stream of nitrogen. After rinsing with heptane, the resulting pasty solid was transferred to a drying dish and subsequently to a vacuum oven pre-heated at 69° C. After 24.5 h of drying under vacuum, the solid was ground in a glass mortar and pestle. The resulting free flowing solid was submitted for impurity analysis, and the solid met all purity specifications. The solid was further dried under vacuum at 69° C. for 96 h to remove residual isopropanol. The solid subsequently met both isopropanol and water content specifications. The title compound was obtained as a white solid (258.7 g; 90.3% assay-corrected yield). $^1$H NMR (500 MHz, MeOD) δ 2.28 (s, 3H), 2.46 (s, 3H), 2.79 (s, 6H), 3.34 (dd, J=5.4, 12.9 Hz, 1H), 3.70 (dd, J=8.9, 12.8 Hz, 1H), 4.35 (dd, J=5.5, 8.7 Hz, 1H), 4.89 (s, 2H), 6.99 (d, J=8.1 Hz, 1H), 7.03 (s, 1H), 7.53 (dd, J=8.4, 14.9 Hz, 4H), 7.73 (d, J=8.1 Hz, 1H), 8.00 (dd, J=3.0, 9.0 Hz, 1H), 8.21 (d, J=6.7 Hz, 1H), 8.34 (d, J=9.1 Hz, 1H), 8.39 (d, J=6.7 Hz, 1H), 8.73 (s, 1H), 9.49 (s, 1H). 13C NMR (125 MHz, MeOD) δ 21.3, 21.9, 39.6, 42.8, 51.5, 66.8, 114.9, 125.3, 125.4, 125.7, 127.5, 129.6, 130.3, 131.7, 131.8, 132.4, 132.9, 133.4, 136.5, 138.6, 141.4, 141.9, 144.2, 146.7, 147.5, 168.6, 172.2. Chiral LC (>99% ee, Chiralpak AS-H). LC-MS (ES+): m/z=454 (M+1), 476 (M+23).

$^1$H NMR (500 MHz, d$_6$-DMSO) δ 2.28 (s, 3H), 2.38 (s, 6H), 2.46 (s, 3H), 3.13 (m, 1H), 3.59 (m, 1H), 4.24 (dd, J=5.2, 8.9 Hz, 1H), 5.28 (s, 2H), 7.08 (d, J=8.07 Hz, 1H), 7.11 (s, 1H), 7.48 (s, 4H), 7.74 (d, J=7.9 Hz, 1H), 7.99 (m, 4H), 8.35 (d, J=6.5 Hz, 1H), 8.45 (d, J=9.1 Hz, 1H), 8.55 (d, J=6.6 Hz, 1H), 8.69 (s, 1H), 9.68 (s, 1H). 13C NMR (125 MHz, d6-DMSO) δ 20.9, 21.2, 40.7, 49.8, 65.4, 113.3, 123.5, 123.8, 123.9, 126.1, 126.6, 126.7, 128.1, 128.6, 130.4, 131.8, 132.2, 132.4, 135.8, 136.2, 139.6, 142.5, 145.2, 146.1, 166.4, 170.5. Chiral LC (>99% ee, Chiralpak AS-H). LC-MS (ES+): m/z=454 (M+1), 476 (M+23).

**di-HCl salt: $^1$H NMR (300 MHz, MeOD) δ 2.25 (s, 3H), 2.43 (s, 3H), 3.05 (m, 1H), 3.4 (m, 1H), 3.98 (dd, J=5.7, 8.4 Hz, 1H), 5.23 (s, 2H), 6.94 (d, J=7.9 Hz, 1H), 6.98 (s, 1H), 7.42 (d, J=8.4 Hz, 2H), 7.48 (d, J=8.4 Hz, 2H), 7.58 (d, J=6.0 Hz, 1H), 7.64 (dd, J=2.1, 9.0 Hz, 1H), 7.70 (d, J=8.1 Hz, 1H), 7.88 (d, J=9.0 Hz, 1H), 8.25 (d, J=6.0 Hz, 1H), 8.31 (s, 1H), 8.98 (s, 1H). 13C NMR (75 MHz, MeOD) δ 21.3, 21.9, 45.3, 55.7, 66.9, 115.3, 122.1, 122.7, 127.0, 127.5, 129.4, 129.8, 129.9, 129.9, 131.8, 133.4, 137.6, 138.4, 138.7, 141.4, 142.2, 143.0, 144.1, 152.3, 168.6, 173.1. Chiral LC (>95% ee, Chiralpak AS-H); LC-MS (ES+): m/z=454 (M+1).

**free base: $^1$H NMR (500 MHz, MeOD) δ 2.25 (s, 3H), 2.44 (s, 3H), 2.98 (dd, J=5.7, 12.9 Hz, 1H), 3.35 (dd, J=8.7, 12.8 Hz, 1H), 3.87 (dd, J=5.7, 8.6 Hz, 1H), 5.23 (s, 2H), 6.94 (d, J=7.9 Hz, 1H), 6.98 (s, 1H), 7.42 (d, J=8.2 Hz, 2H), 7.45 (d, J=8.2 Hz, 2H), 7.59 (d, J=5.9 Hz, 1H), 7.63 (d, 8.9 Hz, 1H), 7.71 (d, J=7.9 Hz, 1H), 7.89 (d, J=9.1 Hz, 1H), 8.25 (d, J=5.9 Hz, 1H), 8.3 (s, 1H), 8.9 (s, 1H). 13C NMR (125 MHz, MeOD) δ 21.3, 21.9, 45.9, 56.8, 66.9, 115.2, 122.0, 122.7, 126.9, 127.5, 127.6, 129.3, 129.8, 129.8, 131.8, 133.4, 137.3, 138.4, 139.2, 141.4, 142.2, 143.0, 144.1, 152.3, 168.6, 173.5.

Example 8. Synthesis of N-Boc-1-aminomethylbenzotriazole

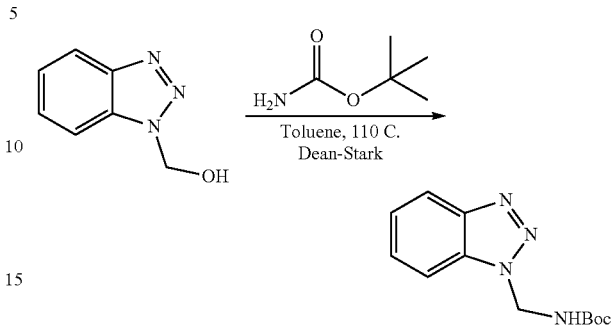

To 1-(hydroxymethyl)benzotriazole (12 g, 80.5 mmol) in toluene (217 mL) was added tert-butyl carbamate (9.4 g, 80.5 mmol) and p-toluenesulfonic acid monohydrate (30.7 mg, 0.2 mmol) and the solution was refluxed (110-120° C.) using Dean-Stark trap for 24 hours. Half of the toluene was evaporated and the solution was cooled to 0° C. and the product was recrystallized. The toluene was then decanted and fresh toluene (50-55 mL) was added. The solution was heated to 100° C. to dissolve and then again cooled to 0° C. Recrystallization gave N-Boc-1-aminomethyl benzotriazole (11.9 g, 60%, 94% pure). Repeated recrystallization (2 times) was carried out to give pure N-Boc-1-aminomethylbenzotriazole (>95% pure, 9.9 g, 50%). $^1$H NMR (500 MHz, d$_6$-DMSO) δ 1.36 (s, 9H), 5.87 (d, J=6.5 Hz, 2H), 7.40 (m, 1H), 7.55 (m, 1H), 7.95 (d, J=8.4 Hz, 1H), 8.03 (d, J=8.4 Hz, 1H), 8.40 (bt, 1H); $^{13}$C NMR (125 MHz, d$_6$-DMSO) δ 27.9, 53.3, 79.2, 111.1, 119.0, 124.1, 127.3, 132.1, 145.4, 155.4. LC-MS (ES+): m/z=249 (M+1), 271 (M+23).

Example 9. Recrystallization of N-Boc-1-aminomethylbenzotriazole

N-Boc-1-aminomethylbenzotriazole (90 g) was dissolved in hot (40±5° C.) acetone (608 mL), filtered (Whatmann 1 filter paper), washed with acetone (2×40 mL), and then concentrated. To the solid, IPA (2×250 mL) was added and concentrated each time. Again IPA (900 mL) was added and the solution was transferred to a 2 L, three neck round bottom flask and heated to 70±5° C. (clear solution). The solution was cooled to room temperature and stirred overnight. A white crystalline precipitate was observed. The mixture was cooled to −40±5° C., and stirred for 30 minutes. The white crystals were filtered, washed with IPA (2×50 mL) and dried under vacuum at room temperature for 1 hour. Then, the crystals were dried at 70±5° C. under vacuum for 48 hours to give 71.1 g (79%) of white crystalline solid.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of synthesizing a compound of Formula (I-a):

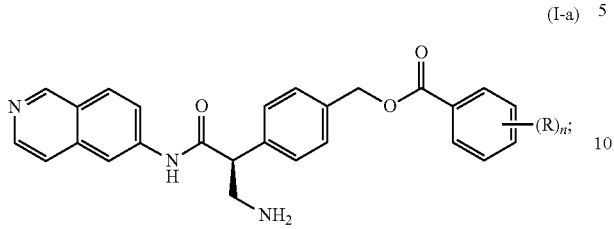
(I-a)

or a pharmaceutically acceptable salt thereof; wherein each R is independently selected from the group consisting of $C_{1-4}$ alkyl, halogen, $C_1$-$C_4$ alkoxy and cyano; and n is an integer from 0 to 3;

comprising:
(a) reacting a compound of Formula (II-a), wherein PG is a nitrogen protecting group,

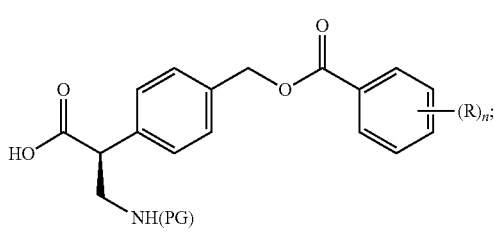
(II-a)

with 6-aminoisoquinoline to form a compound of Formula (III-a)

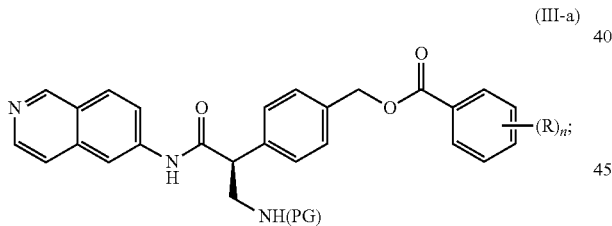
(III-a)

wherein each R is independently selected from the group consisting of $C_{1-4}$ alkyl, halogen, $C_{1-4}$ alkoxy and cyano; and n is an integer from 0 to 3; and (b) removing the nitrogen protecting group to form the compound of Formula (I-a).

2. The method of claim 1, further comprising:
(a) reacting a compound of Formula (IV-a),

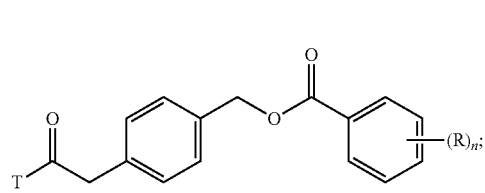
(IV-a)

wherein each R is independently selected from the group consisting of $C_{1-4}$ alkyl, halogen, $C_{1-4}$ alkoxy and cyano; n is an integer from 0 to 3; and T is a chiral auxiliary; with

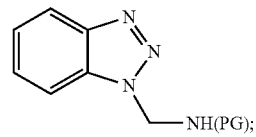

wherein PG is a nitrogen protecting group, in the presence of a base;
to form a compound of Formula (V-a):

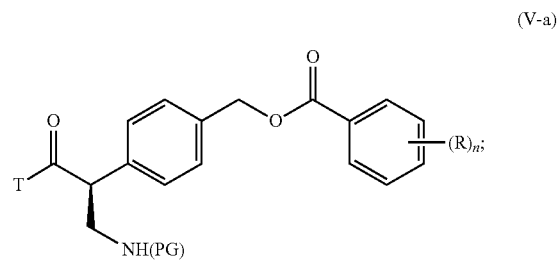
(V-a)

wherein each R is independently selected from the group consisting of $C_{1-4}$ alkyl, halogen, $C_{1-4}$ alkoxy and cyano; n is an integer from 0 to 3; and T is a chiral auxiliary; and (b) removing the chiral auxiliary to form the compound of Formula (II-a).

3. The method of claim 2, further comprising converting a compound of Formula (VIII-a):

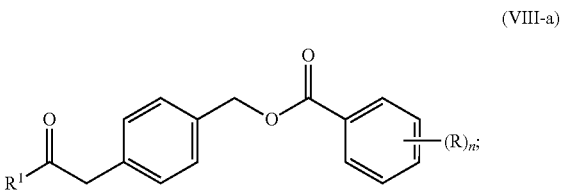
(VIII-a)

wherein each R is independently selected from the group consisting of $C_{1-4}$ alkyl, halogen, $C_{1-4}$ alkoxy and cyano; n is an integer from 0 to 3; and R1 is halogen, $OR^a$, $OC(O)R^b$, $SR^a$, or $SC(O)R^b$; wherein $R^a$ is H, alkyl or aryl, and $R^b$ is alkyl or aryl;
to the compound of Formula (IV-a):

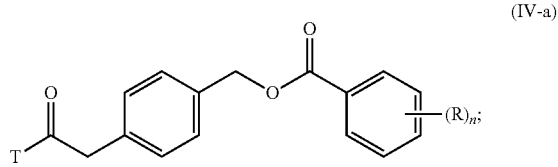
(IV-a)

wherein each R is independently selected from the group consisting of $C_{1-4}$ alkyl, halogen, $C_{1-4}$ alkoxy and cyano; n is an integer from 0 to 3; and T is a chiral auxiliary.

4. The method of claim 3, wherein the compound of Formula (II-a) is synthesized by a method comprising:
(a) reacting

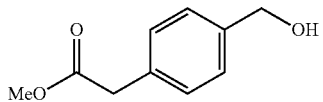

with a compound of Formula (VI-a),

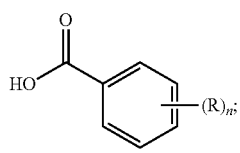
(VI-a)

wherein each R is independently selected from the group consisting of $C_{1-4}$ alkyl, halogen, $C_{1-4}$ alkoxy and cyano; and n is an integer from 0 to 3;
to form a compound of formula (VII-a),

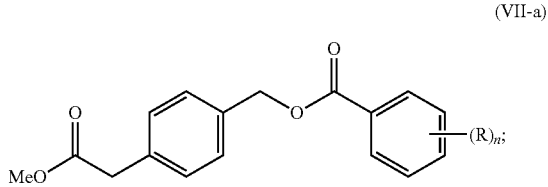
(VII-a)

wherein each R is independently selected from the group consisting of $C_{1-4}$ alkyl, halogen, $C_{1-4}$ alkoxy and cyano; and n is an integer from 0 to 3; and
(b) converting the compound of Formula (VII-a) into the compound of Formula (VIII-a).

5. The method of claim 1, wherein n is 2 and each R is methyl.

6. The method of claim 1, wherein the compound of Formula (I-a) is

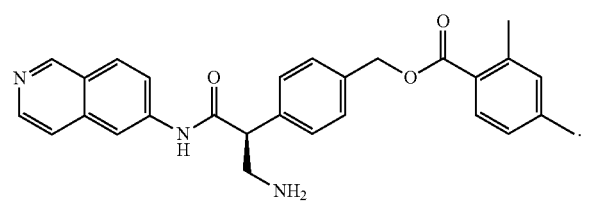 [SMILES: Cc1ccc(C(=O)OCc2ccc([C@@H](CN)C(=O)Nc3ccc4cnccc4c3)cc2)c(C)c1]

7. The method of claim 3, wherein the compound of Formula (VIII-a) is

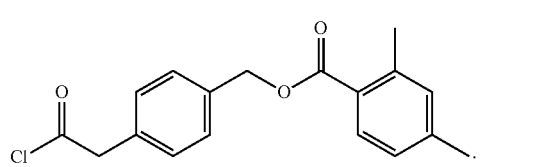 [SMILES: Cc1ccc(C(=O)OCc2ccc(CC(=O)Cl)cc2)c(C)c1]

8. The method of claim 1, wherein n is 0.
9. The method of claim 2, wherein T is

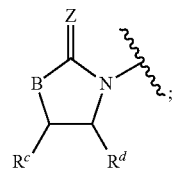

wherein
Z is S or O;
B is S or O;
$R^c$ is hydrogen, $C_{1-4}$ alkyl, or aryl; and
$R^d$ is $C_{1-4}$ alkyl, $C_{3-7}$ branched alkyl; arylalkyl or aryl.

10. The method of claim 9, wherein T is

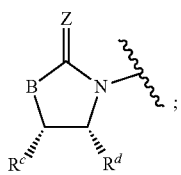

wherein
Z is S or O;
B is S or O;
$R^c$ is hydrogen or aryl; and
$R^d$ is $C_{1-4}$ alkyl, arylalkyl or aryl.

11. The method of claim 10, wherein T is selected from the group consisting of:

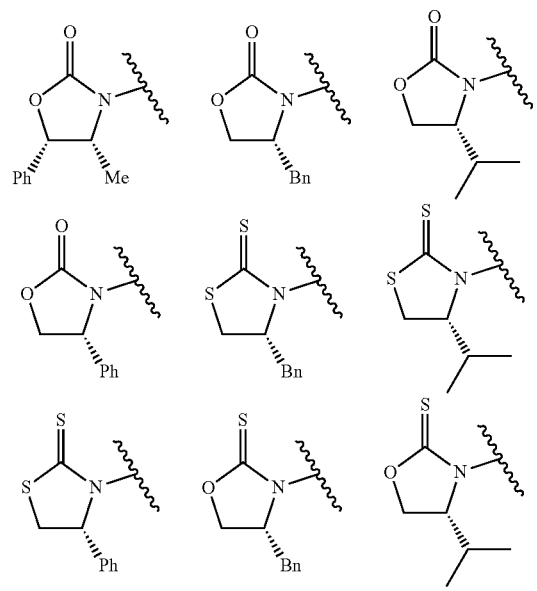

12. The method of claim 11, wherein T is

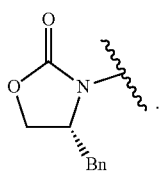

13. A method of synthesizing a compound of the following formula

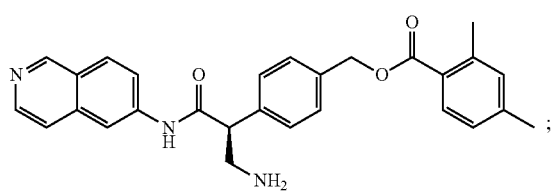 [SMILES: Cc1ccc(C(=O)OCc2ccc([C@@H](CN)C(=O)Nc3ccc4cnccc4c3)cc2)c(C)c1]

or pharmaceutically acceptable salt thereof; comprising:

(a) reacting

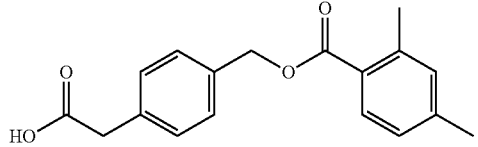 [SMILES: Cc1ccc(C(=O)OCc2ccc(CC(=O)O)cc2)c(C)c1]

with a chlorinating agent, to form an acid chloride;

(b) crystallizing the acid chloride from n-heptane to form a purified acid chloride;

(c) reacting the purified acid chloride with

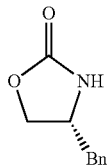

in the presence of a base, to form

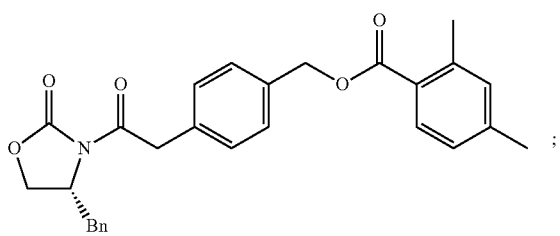 [SMILES: Cc1ccc(C(=O)OCc2ccc(CC(=O)N3C(=O)OC[C@H]3Cc3ccccc3)cc2)c(C)c1]

(d) reacting the product of step (c) with

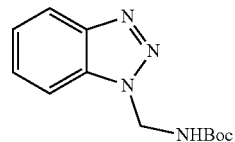 [SMILES: CC(C)(C)OC(=O)NCn1nnc2ccccc21]

in the presence of a base at a temperature between −50° C. and −20° C. to form

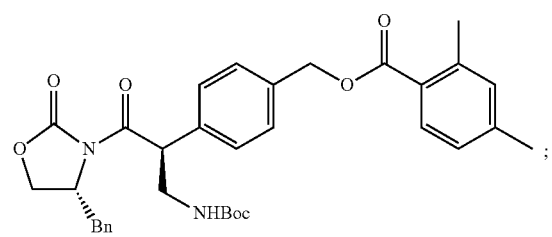 [SMILES: Cc1ccc(C(=O)OCc2ccc([C@@H](CNC(=O)OC(C)(C)C)C(=O)N3C(=O)OC[C@H]3Cc3ccccc3)cc2)c(C)c1]

(e) reacting the product of step (d) with LiOOH to form

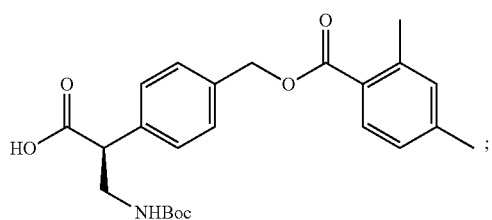 [SMILES: Cc1ccc(C(=O)OCc2ccc([C@@H](CNC(=O)OC(C)(C)C)C(=O)O)cc2)c(C)c1]

(f) recrystallizing the product of step (e) to form a purified product of step (e);

(g) activating the carboxylic acid group of the purified product of step (f) and reacting the activated carboxylic acid with 6-aminoisoquinoline to form

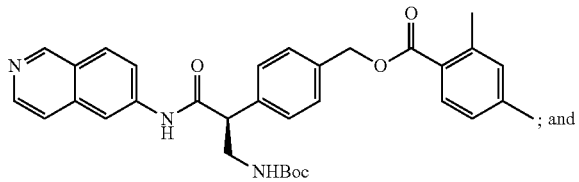 [SMILES: Cc1ccc(C(=O)OCc2ccc([C@@H](CNC(=O)OC(C)(C)C)C(=O)Nc3ccc4cnccc4c3)cc2)c(C)c1]
; and (h) recrystallizing the product of step (g);

(i) reacting the product of step (h) with at least 2 equivalents of MeSO₃H to form

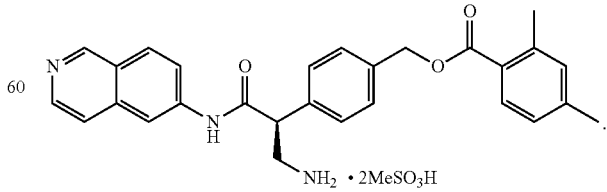

14. The method of claim 13, wherein the chlorinating agent of step (a) is oxalyl chloride or thionyl chloride.

15. The method of claim 13, wherein the base of step (c) is NaH, LiH, KH, nBuLi, secBuLi, LiHMDS, NaHMDS, or KHMDS and step (b) is performed at a temperature between −90° C. and 50° C.

16. The method of claim 13, wherein the base of step (d) is LiHMDS or NaH.

17. The method of claim 13, wherein the LiOOH is formed in situ by lithium hydroxide and hydrogen peroxide.

18. The method of claim 13, wherein the carboxylic acid group is activated in step (g) by addition of trichlorodimethyl ethyl chloroformate and collidine at a temperature of about 0° C.

19. The method of claim 18, wherein the purified product of step (f), 6-aminoisoquinoline, and collidine are mixed followed by addition of trichlorodimethyl ethyl chloroformate.

20. The method of claim 18, wherein the carboxylic acid group is activated by conversion to a mixed anhydride intermediate.

21. A method for the synthesis of the compound of formula (I):

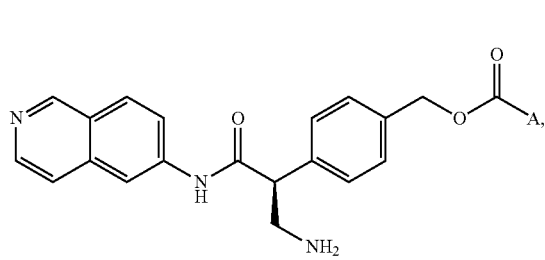

(I)

or a pharmaceutically acceptable salt thereof; wherein A is cyclohexyl or phenyl, substituted with 0-3 substituents independently selected from the group consisting of alkyl, halogen, alkoxy, and cyano comprising
  (a) reacting a compound of Formula (II), wherein PG is a nitrogen protecting group,

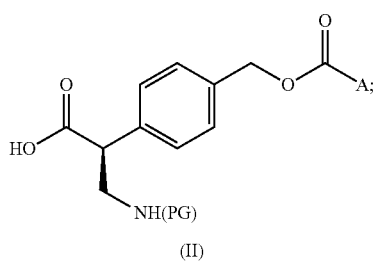

(II)

with 6-aminoisoquinoline to form a compound of Formula (III)

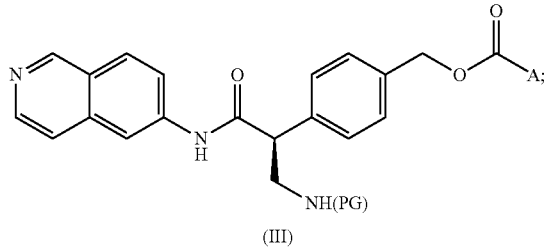

(III)

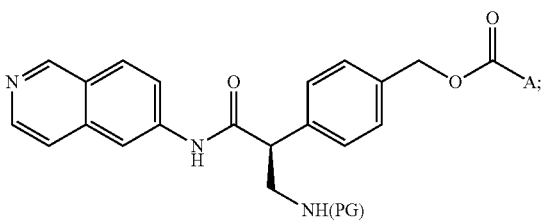

(III)

wherein A is cyclohexyl or phenyl, substituted with 0-3 substituents independently selected from the group consisting of alkyl, halogen, alkoxy, and cyano; and
  (b) removing the nitrogen protecting group to form the compound of Formula (I).

22. A compound selected from the group consisting of

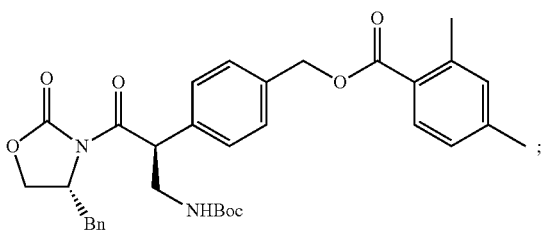

;

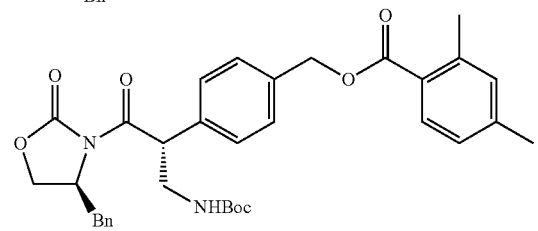

;

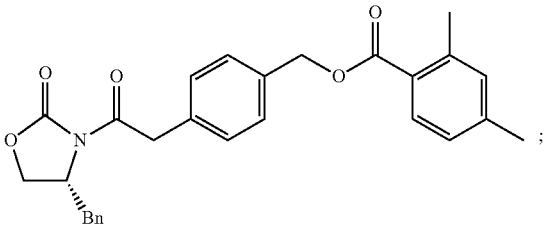

;

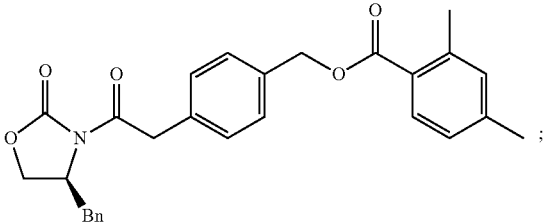

;

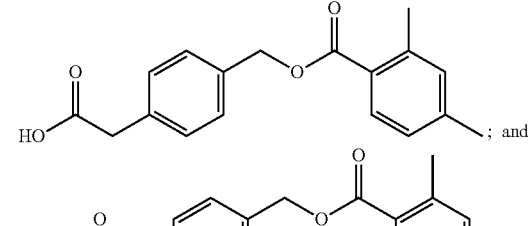

; and

.

* * * * *

UNITED STATES PATENT AND TRADEMARK OFFICE
CERTIFICATE OF CORRECTION

PATENT NO. : 9,643,927 B1
APPLICATION NO. : 14/944101
DATED : May 9, 2017
INVENTOR(S) : Jill M. Sturdivant et al.

Page 1 of 1

It is certified that error appears in the above-identified patent and that said Letters Patent is hereby corrected as shown below:

In the Claims

Column 51, Lines 40–52, Claim 21 replace

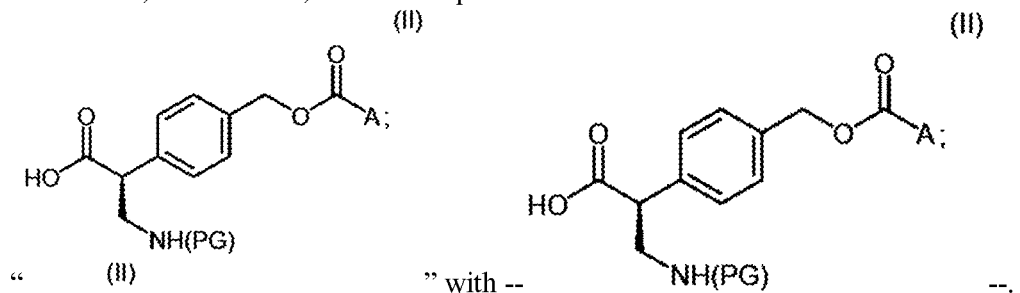

Column 51, Line 56, through Column 52, Line 12, Claim 21 replace

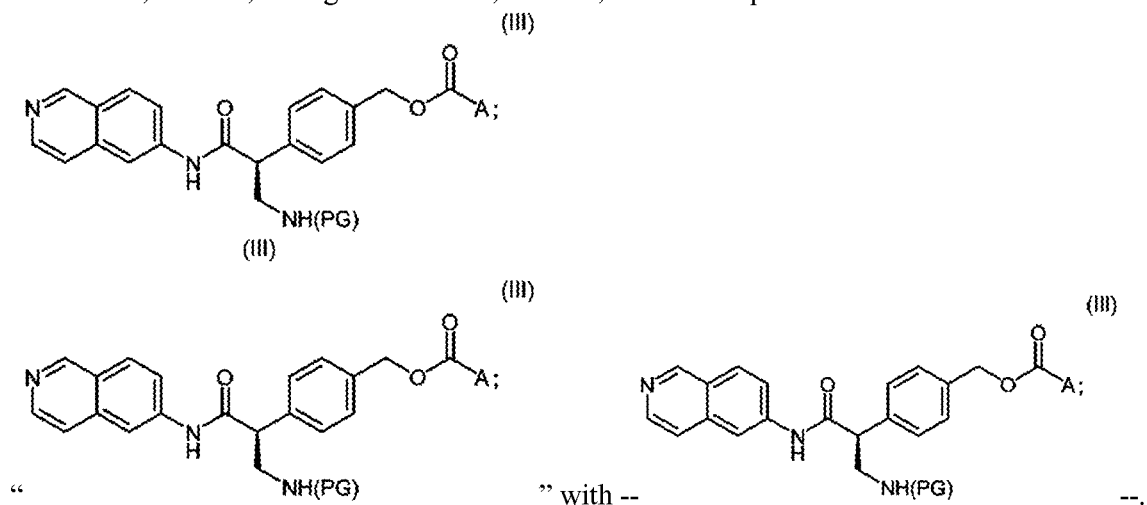

Signed and Sealed this
Tenth Day of July, 2018

Andrei Iancu
*Director of the United States Patent and Trademark Office*